US006348641B1

(12) United States Patent
Stiles et al.

(10) Patent No.: US 6,348,641 B1
(45) Date of Patent: *Feb. 19, 2002

(54) PURIFIED PROTEINS, RECOMBINANT DNA SEQUENCES AND PROCESSES FOR PRODUCING CAFFEINE-FREE BEVERAGES

(75) Inventors: John I. Stiles, Kaneohe; Istefo Moisyadi; Kabi Raj Neupane, both of Honolulu, all of HI (US)

(73) Assignee: University of Hawaii, Honolulu, HI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/165,922

(22) Filed: Oct. 2, 1998

Related U.S. Application Data

(63) Continuation-in-part of application No. 08/622,679, filed on Mar. 26, 1996, now Pat. No. 6,075,184.

(51) Int. Cl.[7] ............ C12N 15/29; C12N 15/54; C12N 15/82; A01H 5/00; A01H 5/10
(52) U.S. Cl. ............ 800/285; 800/278; 800/286; 435/193; 435/320.1; 435/419; 435/468; 536/23.6
(58) Field of Search ................ 800/295, 298, 800/278, 285, 286; 435/419, 468, 193, 320.1; 536/24.1, 23.6

(56) References Cited

U.S. PATENT DOCUMENTS

| 5,296,376 A | 3/1994 | Bridges |
| 5,334,529 A | 8/1994 | Adams et al. |
| 5,364,780 A | 11/1994 | Hershey et al. |
| 5,436,395 A | 7/1995 | Sondahl et al. |
| 5,453,566 A | 9/1995 | Shewmaker et al. |
| 5,457,041 A | 10/1995 | Ginaven et al. |

FOREIGN PATENT DOCUMENTS

| EP | 0 240 208 | 10/1987 |

OTHER PUBLICATIONS

Napoli et al. Plant Cell 2:279–289, Apr. 1990.*
Ecker, J.R. and R.W. Davis, Inhibition of Gene Expression in Plant Cells By Expression of Antisense RNA, *PNAS* (USA) 83: 5372–5376, Aug. 1986.

Smith, C.J.S. et al. Antisense RNA Inhibition of Polygalacturonase Gene Expression in Transgenic Tomatoes, *Nature* 334: 724–726, 1988.

Schulthess B.H. & T.W. Baumann. Are Xanthosine and 7–Methylxanthosine Caffeine Precursors? *Phytochemistry* 39: 1363–1370, 1995.

Hofgen, R. et al. A Visible Marker for Antisense mRNA Experssion in Plants: Inhibition of Chlorophyll Synthesis With a Glutamate–1–Semialdehyde Aminotransferase Antisense Gene. *PNAS* (USA) 91: 1726–1730, 1994.

Ashihara, T.S.H. & G.R. Waller. Review Article Number 68: Purine and Purine Alkaloid Metabolism in *Camellia* and *Coffea* Plants. *Phytochemistry* 31: 2575–2584, 1992.

Spiral, J. & V. Petiard, Development of a transformation method for coffee and regeneration of transgenic coffee plants (Abstract). Colloq. Sci. Int. Cafe [C.R.] 1993, 15th (vol. 1), pp. 115–122.

Schulthess, B.H., Morath, P. and T.W. Baumann. Caffeine biosynthesis starts with the metabolically channelled formation of 7–methyl–XMP—A new hypothesis. Phytochemistry 41 (1):169–175 (1996).

Kato, M. et al. Caffeine biosynthesis in young leaves of *Camellia sinensis:* in vitro studies on N–methyltransferase activity involved in the conversion of xanthosine to caffeine. Physiologia Planatarum 98 (32): 629–636 (1996).

* cited by examiner

*Primary Examiner*—David T. Fox
(74) *Attorney, Agent, or Firm*—Jones, Day, Reavis & Pogue

(57) ABSTRACT

The invention provides purified proteins, DNA sequences that code on expression therefore, and recombinant nucleic acid sequences, including hosts transformed with such sequences, for transforming coffee plants to reduce or eliminate the synthesis of caffeine. Coffee plant cells are transformed by means of transforming vectors that comprise a nucleic acid sequence, operably linked to a transcription promoter in an antisense or sense orientation, that codes on transcription for an RNA that has a length sufficient to interfere with the expression of a specific enzyme in the pathway for caffeine biosynthesis. Coffee plants regenerated from transformed coffee plant cells exhibit caffeine production that has been reduced by up to 98% compared with untransformed coffee plants.

31 Claims, 10 Drawing Sheets

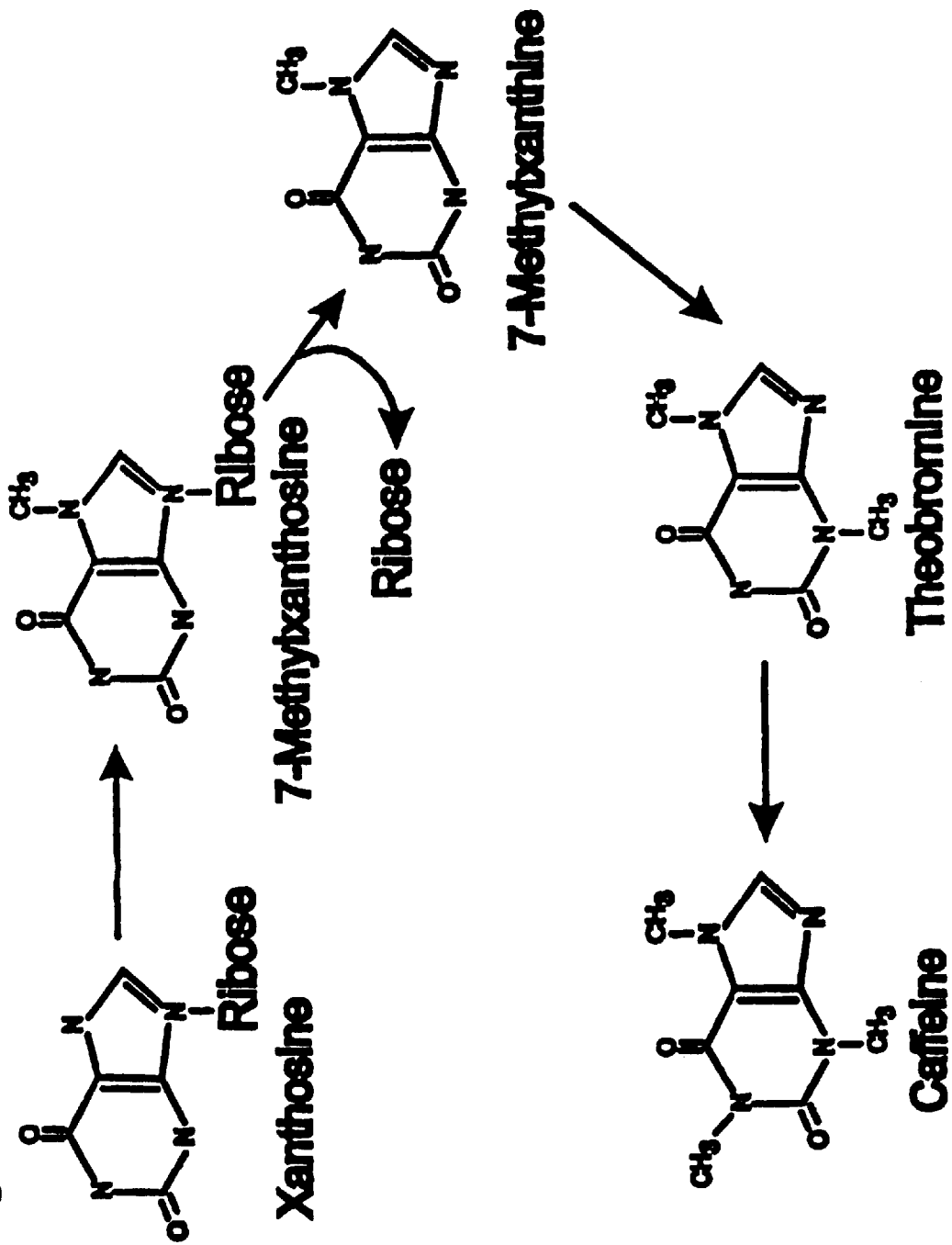
Figure 1. Caffeine Biosynthetic Pathway

Figure 2. Polyacrylamide gel of purified xanthosine-$N^7$-methyl transferase
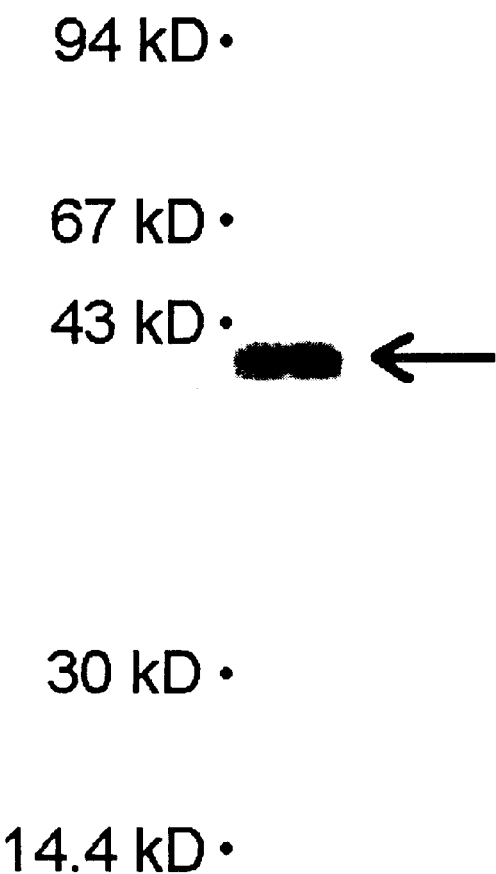

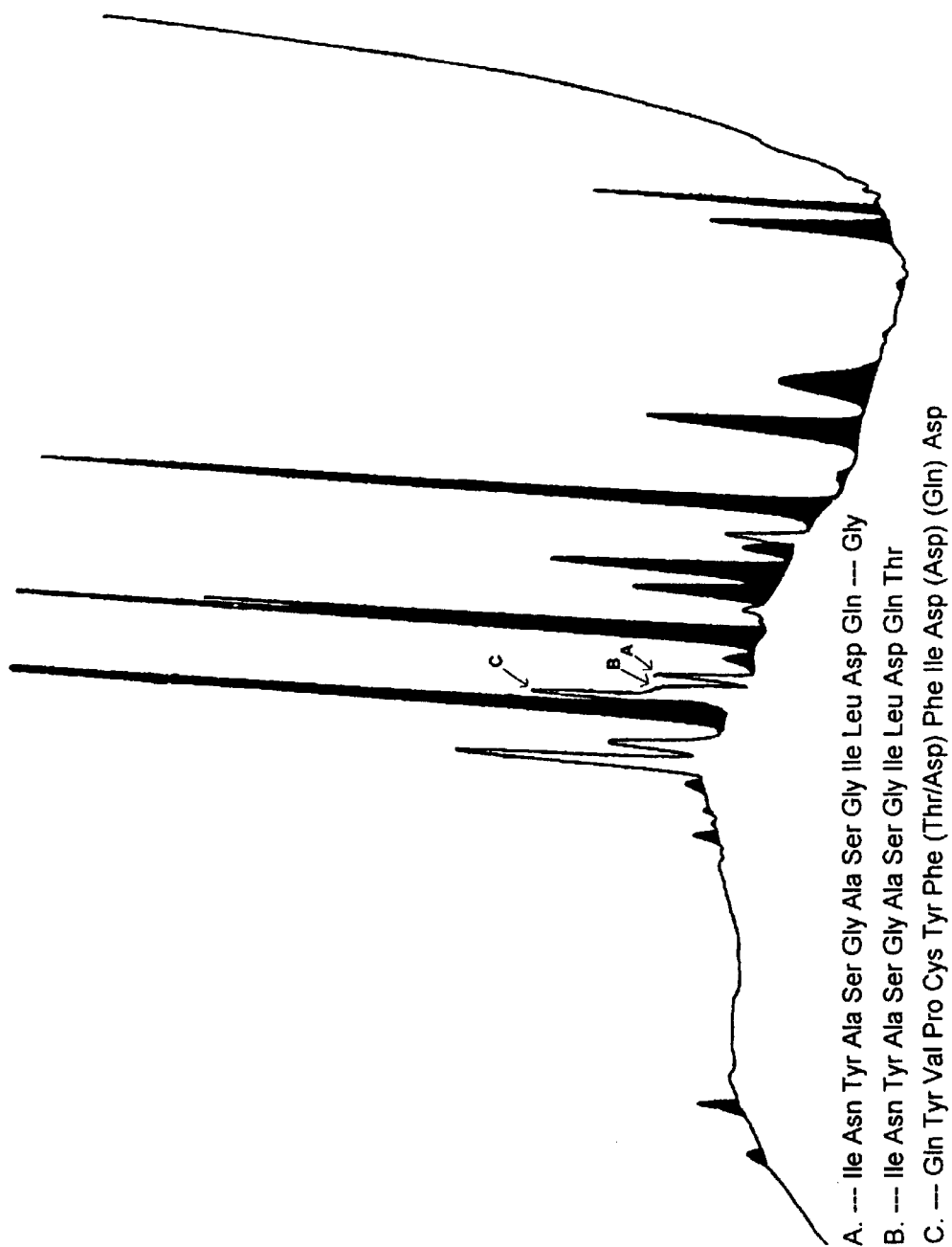
Figure 3. HPLC separation of tryptic digest of xanthosine-N⁷-methyl transferase
A. — Ile Asn Tyr Ala Ser Gly Ala Ser Gly Ile Leu Asp Gln — Gly
B. — Ile Asn Tyr Ala Ser Gly Ala Ser Gly Ile Leu Asp Gln Thr
C. — Gln Tyr Val Pro Cys Tyr Phe (Thr/Asp) Phe Ile Asp (Asp) (Gln) Asp

Figure 4. Oligonucleotides synthesized from peptides

Fragment A. --- Ile Asn Tyr Ala Ser Gly Ala Ser Gly Ile Leu Asp Gln --- Gly
Fragment B. --- Ile Asn Tyr Ala Ser Gly Ala Ser Gly Ile Leu Asp Gln Thr Primer 1    5'ATI AA$_T^C$ TA$_T^C$GCI TCI GGI GC Primer 2    5'ATI AA$_T^C$ TA$_T^C$GCI AG$_T^C$ GGI GC Primer 3    3'TAI TT$_A^G$ AT$_A^G$CGI AGI CCI GC Primer 4    3'TAI TT$_A^G$ AT$_A^G$CGI TC$_A^G$ CCI GC Fragment C. --- Gln Tyr Val Pro Cys Tyr Phe $_{Asp}^{Thr}$ Phe Ile Asp (Asp) (Gln) Asp Primer 5    5'CA$_A^G$ TAT GTI CCI TGT TAT TT Primer 6    3'GTT AT$_A^G$CAI GGI AC$_A^G$ AT$_A^G$AA

FIGURE 5

```
CCTCTGACTT  GCTAAACCTA  CCATTACCTT  TTTCTTCTTG  TCATCTGCAT        50
TCATGGCTTT  TGTAGCCAGG  CAATGGTTTC  TCCTATCCAT  CATTAATGTA       100
GTGGTTGTCT  GTTTCTTGAA  ACCATTTGCC  CTAGGCGAAC  AACAGGTCCC       150
TTGCTACTTC  ATTTTTGGAG  ACTCACAAGA  TGACAATGGC  AACAATAATC       200
ACCTGAACAC  CACTGCCAGG  GCAAATTATC  CACCTTACGG  CATTGATTTC       250
CCAGAAGGTC  CAACTGGTCG  CTTCACCAAT  GGTCGAAATC  ATGCAGACTT       300
CATTGGTGAG  CTCCTTGGAT  TGACAGCTA   CATACCTCCA  TTTGCAAATA       350
CAAAAGGCCG  GGATATCACT  AAAGGCATTA  ATTATGCTTC  GGGAGCATCT       400
GGAATTCTTG  ATCAGACCGG  TCGTCACCTG  GGCGATCTCT  TCAGCTTCAA       450
CGAACAATTG  CACAATCACG  AGAGAGCAAT  TCGCGCATC   GTGCGGTTGA       500
TTGGAAACAG  ATCTGCAACA  AAGAATATC   TAGCCAAATG  TCTGTACACT       550
GTTGCATTGG  GGAATAATGA  TTACATCAAC  AACTACTTGT  TGCCAGAATA       600
TTATCCTACC  AGCCACCTAT  ATACTCCAAG  AGAATTTGCC  AGCTTGTTAA       650
TTAGGCATTA  TTCTCAGCAA  CTACGGACTT  TGTACAGATT  GGGGGCAAGA       700
AAAATAGCCG  TTTTTGGGCT  TGGTTGGCTT  GGCTGCATAC  CTGCTGAGTT       750
ATCTACAGAT  GGTAACTGTG  TGGATTCTAT  TAACGAGGAA  GTTCTGTTAT       800
TCAATGACAA  GCTCAAGCCA  CTGGTTGATG  AACTGAATAC  CGAGTTAAGC       850
GGTGCACAAT  TTCTTTATGT  AGATGTGATA  GCAATCAATT  TGAACAATTT       900
ATCCACCCCT  GCAGAAATTA  CAATTGGCAA  TGCACCATGC  TGCAACGTGT       950
CTGCAGCAGT  TGCTGGTGGA  CAGTGTATTC  CTGGGCAAAT  TCCCTGCAGC      1000
AACAGGAACC  AATATTATTT  TTGGGATGAT  TTCCATCCCA  GTGAAGTAGT      1050
CAATGAAGCA  TATTCAAGAT  TAGCATATTC  TGCGTTATCC  TCATTACTTG      1100
ATGCTGATCC  TCTTGCCATT  GGCGGCCTAA  CAGGCAAAAA  CTGTCATGAT      1150
```

FIGURE 5 (continued)

```
AAAGTGAAGA TACAATAGAC TGTATCTATG TGTCCCATGA TATTTCTATA    1200

TTCCAAGTTT CCGACAAGTC AAACTCAATG TAATAAAACT TGAGAGTCCG    1250

AATGTGCTAG TGTGATGTTA TCTCCTCAAT GGAAACAATA TGTTATCATT    1300

AATCTCAGAC TATTTATAAT TACTATTAAA AAAAAAAAAA AAAAAA        1347
```

FIGURE 6

```
Met Ala Phe Val Ala Arg Gln Trp Phe Leu Leu Ser Ile Ile Asn
 1            5                    10                      15

Val Val Val Val Cys Phe Leu Lys Pro Phe Ala Leu Gly Glu Gln
               20                  25                      30

Gln Val Pro Cys Tyr Phe Ile Phe Gly Asp Ser Gln Asp Asp Asn
               35                  40                      45

Gly Asn Asn Asn His Leu Asn Thr Thr Ala Arg Ala Asn Tyr Pro
               50                  55                      60

Pro Tyr Gly Ile Asp Phe Pro Glu Gly Pro Thr Gly Arg Phe Thr
               65                  70                      75

Asn Gly Arg Asn His Ala Asp Phe Ile Gly Glu Leu Leu Gly Phe
               80                  85                      90

Asp Ser Tyr Ile Pro Pro Phe Ala Asn Thr Lys Gly Arg Asp Ile
               95                 100                     105

Thr Lys Gly Ile Asn Tyr Ala Ser Gly Ala Ser Gly Ile Leu Asp
              110                 115                     120

Gln Thr Gly Arg His Leu Gly Asp Leu Phe Ser Phe Asn Glu Gln
              125                 130                     135

Leu His Asn His Glu Arg Ala Ile Ser Arg Ile Val Arg Leu Ile
              140                 145                     150

Gly Asn Arg Ser Ala Thr Lys Glu Tyr Leu Ala Lys Cys Leu Tyr
              155                 160                     165

Thr Val Ala Leu Gly Asn Asn Asp Tyr Ile Asn Asn Tyr Leu Leu
              170                 175                     180

Pro Glu Tyr Tyr Pro Thr Ser His Leu Tyr Thr Pro Arg Glu Phe
              185                 190                     195

Ala Ser Leu Leu Ile Arg His Tyr Ser Gln Gln Leu Arg Thr Leu
              200                 205                     210

Tyr Arg Leu Gly Ala Arg Lys Ile Ala Val Phe Gly Leu Gly Trp
              215                 220                     225
```

FIGURE 6 (continued)

```
Leu Gly Cys Ile Pro Ala Glu Leu Ser Thr Asp Gly Asn Cys Val
                230                 235                 240

Asp Ser Ile Asn Glu Glu Val Leu Leu Phe Asn Asp Lys Leu Lys
                245                 250                 255

Pro Leu Val Asp Glu Leu Asn Thr Glu Leu Ser Gly Ala Gln Phe
                260                 265                 270

Leu Tyr Val Asp Val Ile Ala Ile Asn Leu Asn Asn Leu Ser Thr
                275                 280                 285

Pro Ala Glu Ile Thr Ile Gly Asn Ala Pro Cys Cys Asn Val Ser
                290                 295                 300

Ala Ala Val Ala Gly Gly Gln Cys Ile Pro Gly Gln Ile Pro Cys
                305                 310                 315

Ser Asn Arg Asn Gln Tyr Tyr Phe Trp Asp Asp Phe His Pro Ser
                320                 325                 330

Glu Val Val Asn Glu Ala Tyr Ser Arg Leu Ala Tyr Ser Ala Leu
                335                 340                 345

Ser Ser Leu Leu Asp Ala Asp Pro Leu Ala Ile Gly Gly Leu Thr
                350                 355                 360

Gly Lys Asn Cys His Asp Lys Val Lys Ile Gln
                365                 370
```

PURIFIED PROTEINS, RECOMBINANT DNA SEQUENCES AND PROCESSES FOR PRODUCING CAFFEINE-FREE BEVERAGES

This application is a continuation-in-part of U.S. patent application, Ser. No. 08/622,679, filed Mar. 26, 1996, now U.S. Pat. No. 6,075,184.

BACKGROUND OF THE INVENTION

The invention relates to purified proteins, recombinant nucleic acid sequences, hosts transformed with such sequences, and processes for producing caffeine-free or caffeine-reduced beverages. More particularly, the invention provides recombinant nucleic sequences that suppress the expression of caffeine in coffee plants and in coffee beans harvested from them.

Coffee is prepared from the roasted ground beans of the plants of the genus Coffea, generally from the species *Coffea arabica* (arabica coffee), *Coffea canephora* (robusta coffee), and the like. Coffee plants produce the alkaloid caffeine, which is present in their dried fruit, coffee beans. Because many coffee drinkers prefer coffee without caffeine, a number of processes have been developed to remove caffeine from coffee beans. However, all of these processes also result in the removal of substances other than caffeine from the beans, thereby adversely affecting the taste of coffee brewed from the treated beans. Although a few naturally occurring caffeine-free coffees and related genera are known (Mascarocoffea spp. and *Coffea bengalensis*), they have no commercial value. (Charrier and Berthaud (1975), "Variation Of Caffeine Content In The Coffea Genus", Cafe' Cacao The', 14:251–264). Accordingly, there is a need for a method for producing decaffeinated coffee beans that does not result in the removal of substances from the beans other than caffeine.

Caffeine is a naturally occurring purine alkaloid produced by coffee and tea plants, among others. It is believed that caffeine synthesis protects the plants from insects. Coffee plants synthesize caffeine from the nucleoside xanthosine in four sequential reactions as shown in FIG. 1. (For a review, see Suzuki, T., Ashihara, H. and Waller, G. R. (1992), *Phytochemistry* 31: 2575). The first step in the pathway is the methylation of the nucleoside xanthosine by S-adenosylmethionine, which is catalyzed by the enzyme xanthosine-$N^7$-methyltransferase (XMT). The product, 7-methylxanthosine, is hydrolyzed (a ribose is removed) to 7-methylxanthine, and undergoes further methylations to theobromine and caffeine. It is to be expected that interruption of this sequence of synthetic reactions would block caffeine synthesis. Accordingly, a strategy for selectively reducing or eliminating caffeine from coffee plants is to inhibit or eliminate synthesis of specific enzymes in the pathway for caffeine biosynthesis.

In one embodiment, this invention relates to genetic alteration of coffee plants to inhibit or eliminate synthesis of XMT. In the preferred embodiments, synthesis of XMT is suppressed by transforming coffee plant cells with a nucleic acid sequence that codes on transcription for an RNA that is either sense or antisense to the messenger RNA (mRNA) that codes on expression for XMT.

It is expected that the invention can be used to suppress caffeine synthesis in tea (genus Camellia, e.g., *Camellia sinensis*) and cola (genus Cola, e.g., *Cola acuminata*), as well as related alkaloids in chocolate (genus Theobroma, e.g., *Theobroma cacao*). Thus, the invention may be generalized to produce other caffeine-free beverages and food products, including tea, cocoa, and other chocolate-based beverages or foods.

SUMMARY OF THE INVENTION

The invention provides purified proteins, DNA sequences that code on expression therefore, and recombinant DNA sequences, including hosts transformed with such sequences, for transforming coffee plants to reduce or eliminate the synthesis of caffeine. The DNA sequences are characterized in that they code on expression for an enzyme, xanthosine-$N^7$-methyltransferase (XMT), that is the first step in the pathway for caffeine synthesis in coffee. The base sequence of that DNA and the predicted amino acid sequence of XMT is provided.

In one embodiment of the invention, coffee plant cells are transformed by means of transforming vectors that comprise a transcriptional initiation region (promoter) operably linked to a nucleic acid sequence that codes on transcription for an RNA that is complementary (antisense) to a mRNA that codes for at least one enzyme in the pathway for caffeine biosynthesis, the transcribed RNA having a length sufficient to interfere with the expression of the enzyme. In another embodiment of the invention, coffee plant cells are transformed by means of transforming vectors that comprise a nucleic acid sequence that codes on transcription for an RNA that shows substantial homology (sense) to a mRNA that codes for the enzyme, and that has a length sufficient to interfere with the expression of the enzyme.

Thus, for example, coffee plant cells may be transformed with a nucleic acid sequence that codes for an RNA that is sense or antsense to the mRNA for XMT, the enzyme active in the first step of the pathway for caffeine synthesis. Expression of either sense or antisense nucleic acid sequences in the transformed cells suppresses or eliminates the production of caffeine, although other aspects of cellular metabolism are not affected.

By the method of the invention, transformed coffee plant cells have been obtained in which caffeine production has been reduced by up to 98% compared with untransformed coffee plant cells. The invention also provides coffee plants regenerated from such transformed coffee plant cells, and coffee beans from these coffee plants.

A feature of the invention is that individual transformed coffee plants can be selected that produce, for example, no caffeine, or 1%, 2%, 10%, 25%, 50%, 75%, 90% of the normal amount of caffeine. Thus, "decaffeinated" coffee could include "100% decaf", "99% decaf", "98% decaf", 90% decaf, "75% decaf", "50% decaf", "25% decaf", "10% decaf", or the like. The generally accepted level of caffeine for a coffee to be called "decaffeinated" is less than 2% to 3% of the normal amount of caffeine. Thus, the transformed coffee plant cell preferably exhibits greater than 98% reduction in caffeine.

BRIEF DESCRIPTION OF THE DRAWINGS

FIG. 1 is a schematic drawing of the pathway for caffeine synthesis in *Coffea arabica*.

FIG. 2 is a photograph of a silver stained SDS PAGE gel of purified xanthosine-$N^7$-methyltransferase.

FIG. 3 is a densitometric plot showing elution of tryptic fragments of purified xanthosine-$N^7$-methyltransferase following HPLC separation.

FIG. 4 is a description of the oligonucleotide primers used to screen the cDNA library cDNA encoding xanthosine-$N^7$-methyltransferase.

FIG. 5 is the base sequence of the cDNA that encodes xanthosine-$N^7$-methyltransferase.

FIG. 6 is the predicted amino acid sequence of xanthosine-$N^7$-methyltransferase.

DETAILED DESCRIPTION OF THE INVENTION

DEFINITIONS

Figure 7:
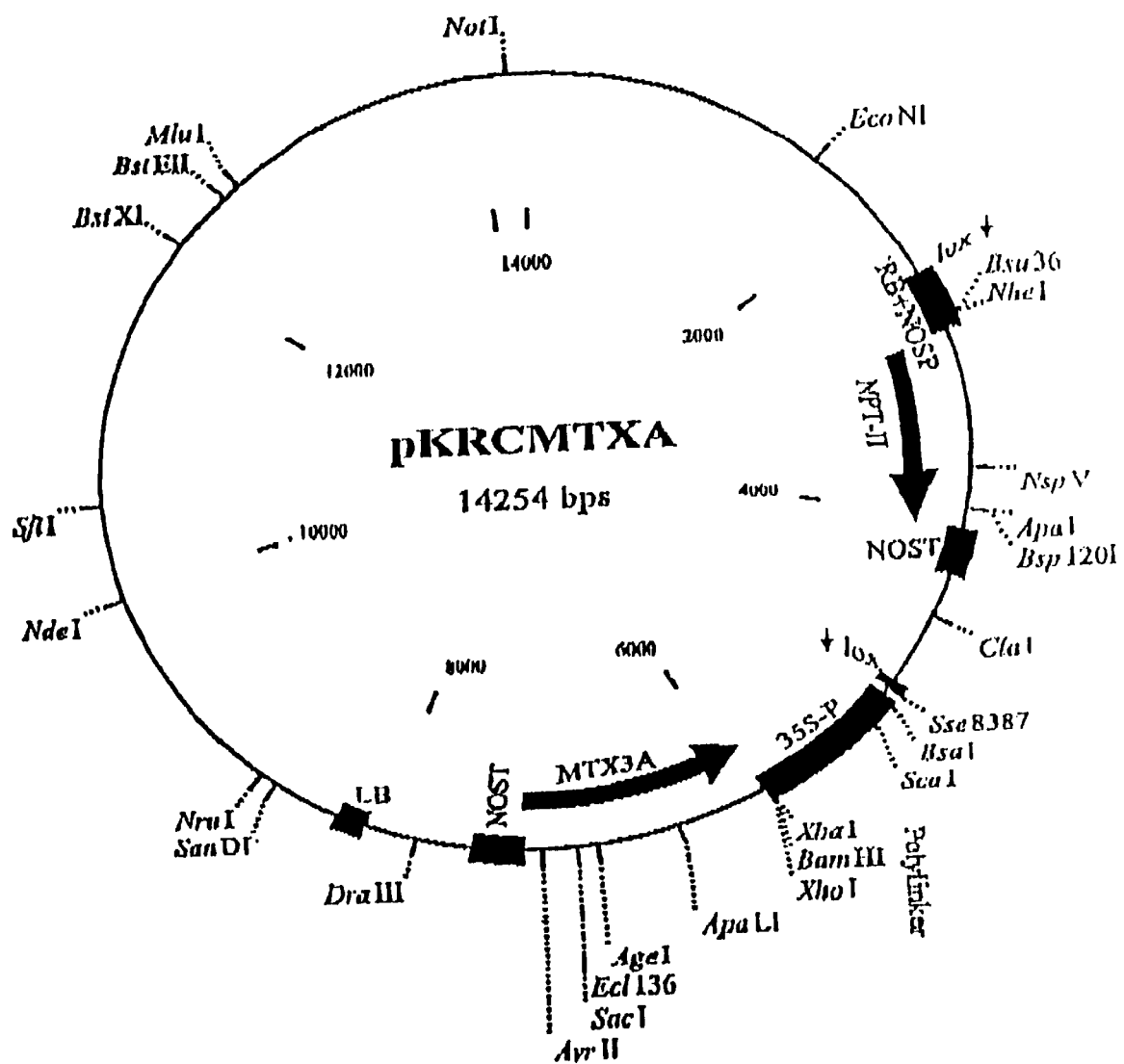
FIG. 7 is a schematic illustration showing the construction of the plasmid pKRCMTX-A by the insertion of xanthosine-$N^7$-methyltransferase cDNA (in the antisense orientation) into the pKR1 transformation vector. NOS=nopaline synthase; CaMV=cauliflower mosaic virus; GUS=β-glucuronidase; and NPT II=neomycin phosphotransferase II.

To facilitate understanding of the invention, a number of terms are defined below.

Nucleotide—A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is called a nudeoside. The base characterizes the nucleotide. The four DNA bases are adenine ("A"), guanine ("G"), cytosine ("C"), and thymine ("T"). The four RNA bases are A, G, C, and uracil ("U").

DNA Sequence—A linear array of nucleotides connected one to the other by phosphodiester bonds between the 3' and 5' carbons of adjacent pentoses.

Codon—A DNA sequence of three nucleotides (a triplet) which encodes through mRNA an amino acid, a translation start signal or a translation termination signal. For example, the nucleotide triplets TTA, TTG, CTT, CTC, CTA and CTG encode for the amino acid leucine ("Leu"), TAG, TM and TGA are translation stop signals and ATG is a translation start signal, which also encodes the amino acid methionine ("MET").

Polypeptide—A linear array of amino acids connected one to the other by peptide bonds between the amino and carboxy groups of adjacent amino acids.

Genome—The entire DNA of a cell or a virus. It includes inter alia the structural gene coding for the polypeptides of the substance, as well as promoter, transcription and translation initiation and termination sites.

Gene—A DNA sequence which encodes through its template or messenger RNA ("mRNA") a sequence of amino acids characteristic of a specific polypeptide.

Transcription—The process of producing mRNA from a gene or DNA sequence.

Translation—The process of producing a polypeptide from mRNA.

Expression—The process undergone by a gene or DNA sequence to produce a polypeptide. It is a combination of transcription and translation.

Antisense—The term "antisense", as used herein, is used in reference to RNA sequences which are complementary to a specific RNA sequence (e.g., mRNA). Antisense RNA may be produced by any method, including synthesis by splicing nucleic acid sequences that code for all or part of the specific RNA sequence in a reverse (inverted) orientation to a promoter which permits the synthesis of a coding sequence.

Sense—The term "sense", as used herein, is used in reference to a substantial run of RNA bases having essentially the same base sequence as a specific RNA sequence (e.g., mRNA). Sense RNA may be produced by any method, including synthesis by splicing nucleic acid sequences that code for all or part of the specific RNA sequence in a sense orientation to a promoter which permits the synthesis of a coding sequence.

Plasmid—A nonchromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for tetracydine resistance (TETR) transforms a cell previously sensitive to tetracycline into one which is resistant to it. A cell transformed by a plasmid is called a "transformant."

Phage or Bacteriophage—A bacterial virus, many of which consist of DNA sequences encapsidated in a protein envelope or coat ("capsid").

Cloning Vehicle—A plasmid, phage DNA, cosmid or other DNA sequence which is able to replicate in a host cell, characterized by one or a small number of endonuclease recognition sites at which such DNA sequences may be cut in a determinable fashion without attendant loss of an essential biological function of the DNA, e.g., replication, production of coat proteins or loss of promoter or binding sites, and which contain a marker suitable for use in the identification of transformed cells, e.g., tetracycline resistance or ampicillin resistance. A cloning vehicle is often called a vector.

Cloning—The process of obtaining a population of organisms or DNA sequences derived from one such organism or sequence by asexual reproduction.

Recombinant DNA Molecule or Hybrid DNA—A molecule consisting of segments of DNA from different genomes which have been joined end-to-end outside of living cells and able to be maintained in living cells.

cDNA—A DNA strand complementary to an mRNA that codes for a particular polypeptide.

The invention strategy for selectively reducing or eliminating caffeine from coffee plants is to inhibit or eliminate synthesis of specific enzymes in the pathway for caffeine biosynthesis by suppression with antisense RNA or co-suppression with sense RNA. Although the strategy may be generalized to other enzymes in the pathway for caffeine synthesis in coffee plants and other caffeine-producing plants, in the presently preferred embodiments of this invention the expression of the first unique enzyme in the pathway, xanthosine-$N^7$-methyltransferase (XMT), is suppressed. While the role of XMT in caffeine synthesis has been elucidated by radiolabeling of precursors, to this date the enzyme has not been purified nor has its amino acid sequence been determined. This invention therefore includes substantially purified XMT. The invention further includes the amino acid sequence of tryptic fragments isolated from the purified XMT.

Suppression of Enzyme Expression in Transformed Coffee Plants

In general, to produce an antisense RNA transcript, nucleic acid sequences derived from the gene (or a naturally occurring allelic variant of the gene) whose expression is to be reduced (e.g., XMT), are placed downstream of a transcription promoter in the opposite transcriptional orientation relative to the direction of transcription of the endogenous gene present in the chromosome. The resulting antisense construct is introduced into the plant cell where the antisense construct directs the transcription of antisense RNA transcripts. The antisense RNA transcript is complementary to the sense transcript produced by the endogenous gene in the plant. While not limiting the invention to any particular theory, it is believed that the antisense transcripts may form a duplex with the sense RNA transcripts or may interfere with transcription of the endogenous gene, thereby preventing the transcription, splicing and/or translation of the sense (or endogenous RNA) transcript. Regardless of the mechanism involved, a reduction in the functioning of the naturally existing RNA is achieved.

Inhibition or suppression of gene expression in plants can also be achieved by the introduction of nucleic acid sequences which direct the expression of "sense" transcripts which correspond to endogenously expressed RNA transcripts. This phenomenon, known as "co-suppression" is well known and co-suppression of a number of plant genes has been reported. Co-suppression or sense suppression may involve the coordinate repression (silencing) of a transgene and a homologous endogenous gene, or the repression of two homologous transgenes. While the invention is not limited to a particular theory, it is believed that co-suppression may involve post-transcriptional events such as the induction of RNA degradation by the overexpression of a given transcript, due to expression of both the endogenous RNA and the transgene RNA transcripts. Additionally, the interaction of the transgene and the endogenous gene may occur on a DNA-DNA level which may result in the methylation of the gene sequences; methylated gene sequences are often transcriptionally inactive in plants.

Whether suppression of the expression of an endogenous gene is by antisense RNA or by co-suppression with sense RNA, it has been reported that it is not necessary to transform plant cells with a DNA construct that is as long as the relevant mRNA produced by the cell. (See, e.g., WO 91/01375, where DNA constructs containing a DNA sequence encoding RNA complementary to "a substantial run of bases" showing substantial homology to a mRNA encoding an enzyme involved in ethylene biosynthesis were produced and used to suppress ethylene biosynthesis in tomatoes.) Furthermore, the nucleic acid segment to be introduced in antisense suppression generally will be substantially identical to at least a portion of the endogenous gene or genes to be repressed, but need not be identical. The transforming vectors of the present invention can be designed such that the inhibitory effect applies to other proteins within a family of genes exhibiting homology or substantial homology to the target gene. Segments from a gene can be used (i) directly to inhibit expression of homologous genes in different plant species, or (ii) as a means to obtain the corresponding sequences, which can be used to suppress the gene.

The introduced sequence also need not be full length relative to either the primary transcription product or fully processed mRNA. Generally, higher homology can be used to compensate for the use of a shorter sequence. Furthermore, the introduced sequence need not have the same intron or exon pattern and homology of non-coding segments will be equally effective. Preferably, the DNA constructs comprise a base sequence at least 30 or 40 to about 2000 nucleotides in length for transcription into antisense or sense RNA. It is preferred to use sequences at least 100 nucleotides in length and, more preferably, at least about 200 nucleotides in length. There is no theoretical upper limit to the base sequence; it may be as long as the relevant mRNA produced by the cell.

The choice of the transcription promoter in the nucleic acid construct depends on the type of host cell to be utilized. Promoters which are active in plant cells include the octopine synthase promoter, the nopaline synthase promoter and the mannopine synthase promoter from the Ti plasmid, ORF7, the 35S promoter from cauliflower mosaic virus (CaMV), the double 35S promoter (D35S), the ribulose-1, 3-biphosphate carboxylase small subunit promoter, and the phasolin promoter. Other promoters active in plant cells are known in the art.

Transforming vectors containing the nucleic acid sequences can be introduced ti into plant cells by a variety of published techniques known to those skilled in the art. Exemplary techniques are microprojectile (biolistic) bombardment, co-cultivation with a plasmid-containing bacteria such as *Agrobacterium tumefaciens*, direct DNA uptake by protoplasts (often enhanced by the use of polyethylene glycol or electroporation), electrophoresis, microinjection, silicon carbide fibers, and the like.

A large number of vectors are available for replication in bacterial hosts. A number of these vectors are commercially available, such as λgt10 and 11, the pUC series, M13 series, pBR322, pACYC184, or the like. The selection of vector will be dependent upon convenience of preparation, availability, copy number, size, and the like.

Suppression of XMT Synthesis

To obtain nucleic acid sequences that code on transcription for all or part of the mRNA that codes for the enzyme XMT, cDNA probes based on portions of the amino acid sequence obtained from samples of the purified enzyme were synthesized and a portion of the gene was amplified using the polymerase chain reaction (PCR). The PCR products were used to screen a cDNA library synthesized from young leaf mRNA to identify transcripts encoding XMT. The positive transcripts were sequenced and approximately 90% of the gene encoding XMT was obtained.

The cDNA sequence that codes for XMT mRNA was amplified using PCR and incorporated into a transformation vector which included an antibiotic resistance gene. Insertion of the cDNA sequence into the vector was either in a sense direction or in an antsense direction. The constructs were used to transform coffee plant leaf tissue which was then placed into tissue culture for development of callus. Presumptive successful incorporation of either vector into coffee plant cells was determined by growth of the cells in the presence of the antibiotic (e.g., kanamycin).

Caffeine production by transformed and untransformed (control) callus cell cultures was determined by assaying the caffeine exuded into the culture medium. Transformed callus cultures exhibiting reduced levels or no caffeine production were selected for further culture and induction of embryonic tissue. When sufficient tissue is obtained, the presence of the DNA construct in the genome of the plant cells was confirmed by PCR analysis.

The transformed embryos were thereafter grown into novel coffee plants in which caffeine production is partially inhibited or substantially eliminated. Naturally decaffeinated or partially decaffeinated coffee is prepared from roasted ground fruit from these novel plants.

A feature of the invention is that individual transformed embryos may be selected based on the level of caffeine produced. Thus, transformed coffee plants can be obtained that produce no caffeine or, for example, as described previously, produce no caffeine, or less than 2%, 10%, 25%, 50%, 75%, or the like, of the normal amount of caffeine. Thus, decaffeinated coffee would include "100% decaf", "98% decaf", "90% decaf", "75% decaf", "50% decaf", "25% decaf", or the like.

Specific Embodiments of the Invention

Fresh leaf tissue from young leaves of *C. arabica* was macerated and protein extracted therefrom. Column purified extracts were assayed for enzymatic activity, by monitoring the methylation of xanthosine using $C^{14}$ labeled S-adenosylmethionine as substrate. The reaction product was confirmed as 7-methylxanthosine by comparing the migration of the labeled reaction product with migration of 3-methylxanthine, 7-methylxanthine, 8-methylxanthine, 7-methylxanthosine, xanthine and xanthosine in each of four different chromatography systems.

The purity of the protein isolates was determined using SDS PAGE electrophoresis and two dimensional gel electrophoresis. Silver staining of one dimensional SDS PAGE gels indicated the presence of a doublet with the enzymatic activity of XMT, with a molecular weight of 36–37 kD as shown in FIG. 2. Each protein was further resolved with isoelectric focusing. The data indicates the presence of isozymes of XMT that may result from post translational modification of the protein; alternatively, there may be a gene family encoding XMT enzymes.

The doublet visualized on SDS PAGE gels was used for protein sequencing. Purified XMT was subjected to partial tryptic digestion to create fragments for further analysis; three peaks were resolved using HPLC. Sequencing was performed by the Protein Structure Laboratory of the University of California, Davis using automated Edman degradation. (Edman, P. and Begg, G., *Eur. J. Biochem.* 1:80). Two unique sequences were resolved, and used to construct primers for probe synthesis. RNA was extracted from coffee leaves. mRNA containing poly ($A^+$) sequences was purified therefrom. A cDNA library was prepared from the poly ($A^+$) mRNA using reverse transcriptase. Double stranded DNA was prepared using DNA polymerase I, and recovered by precipitation. The cDNA was fractionated and inserted into phage for amplification. The cDNA library was screened with a PCR synthesized probe produced using primers based on the DNA sequence expected from the amino acid sequence of the purified XMT. A clone producing a cDNA containing the sequences coding for XMT has been identified.

The cDNA corresponding to the gene encoding XMT was used to transform coffee plant leaf tissue. A modified pBI-121 plasmid (pKR1) was used as a transforming vector.

In one embodiment of the invention, the sequences corresponding to DNA that codes on expression for XMT were inserted into the plasmid in an inverted orientation adjacent to a cauliflower mosaic virus 35S promoter to form the DNA construct "pKRCMTXA", illustrated in FIG. 7. RNA transcribed therefrom is complementary (antisense) to all or part of the mRNA that encodes the amino acid sequence of XMT.

Figure 8:
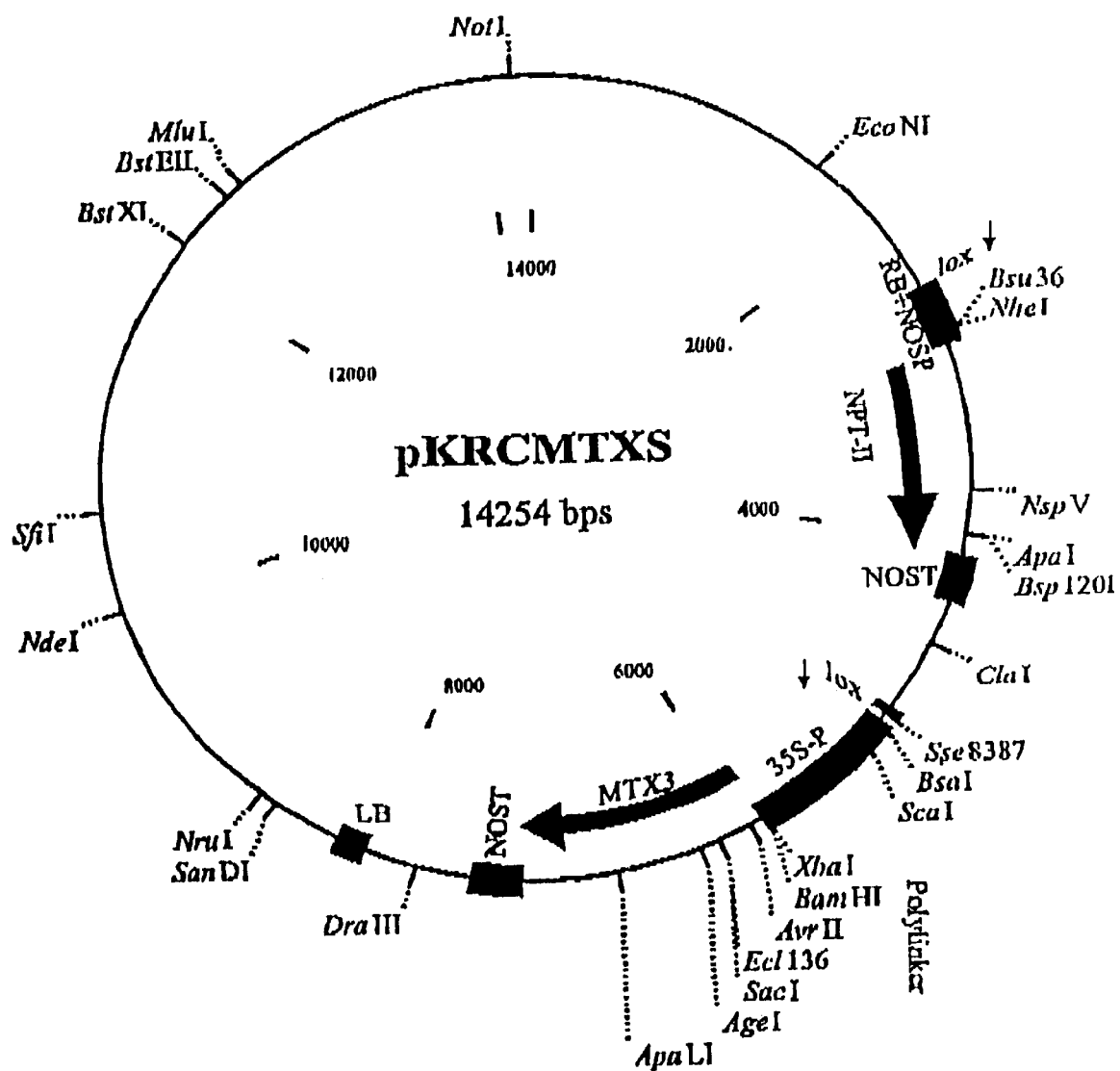
FIG. 8 is a schematic illustration showing the construction of the plasmid pKRMTX-S by the insertion of xanthosine-$N^7$-methyltransferase cDNA in the sense orientation into the pKR1 transformation vector. NOS=nopaline synthase; CaMV=cauliflower mosaic virus; GUS=β-glucuronidase; and NPT II=neomycin phosphotransferase II.

In another embodiment of the invention, the sequences corresponding to the DNA coding on expression for XMT was inserted into the plasmid in a sense orientation adjacent to the cauliflower mosaic virus 35S promoter to form the DNA construct "pKRCMTXS", illustrated in FIG. 8. RNA transcribed therefrom has substantially the same base sequence as all or part of the mRNA that encodes the amino acid sequence of XMT.

Complete plasmid vector constructs were amplified in bacterial hosts. The hosts were disrupted and the amplified plasmid vectors were electroporated into a strain of *Agrobactetium tumefaciens*. Confirmation of the presence and orientation of the XMT cDNA insert in the Agrobacteria was determined by PCR.

Mature young coffee leaves from plagiotrophic coffee plant shoots were co-cultivated with the transformed Agrobacteria to establish infection and transfer of the plasmid vector. The leaf tissue was then transferred into callus induction medium containing kanamycin until the appearance of primary callus. The antibiotic resistant cells were then transferred to embryo induction media.

Caffeine content in the culture media of transformed callus cell lines and untransformed control callus cell lines was determined by HPLC. Some of the transformed cell lines were found to have only 2% of the normal level of caffeine found in regular plants. Thus, expression of the XMT gene appears to have been silenced by the introduction of the antisense cDNA.

EXAMPLES

A. Purification of Xanthosine-$N^7$-methyltransferase from *C. arabica* L. cv Guatemalan Coffee Leaves.

Young leaf tissue, less than 5 mm in length (equivalent to the B3 stage (Frischknecht, P. M., Ulmer-Dufek, J. and Baumann, T. W. (1986) *Phytochemistry* 25:613) were collected from trees grown at the University of Hawaii Waimanalo Research Station, Oahu, Hawaii. Leaves were immediately immersed in liquid nitrogen (liquid $N_2$) and stored at −70° C. until used. All subsequent procedures were carried out at 4° C. unless otherwise stated. Leaf tissue (150 g) was macerated in a mortar and pestle under liquid $N_2$ and, while still frozen, transferred to a pre-chilled domestic coffee grinder and ground with a small piece of dry ice for about 30 sec. The powdered tissue was added to a beaker containing 1.5 L of ice cold 80% acetone, 5 mM thiourea, and 12.5 mM β-mercaptoethanol. After mixing on a magnetic stirrer for 45 min, the tissue was recovered by filtration under vacuum in a Buchner funnel containing Whatman No. 1 filter paper. The tissue was washed with 2.5 L of 80% ice cold acetone containing thiourea and β-mercaptoethanol as above, air dried for 20 min and then lyophilized for 48 hours.

The resulting acetone powder was homogenized in a blender with 400 mL of extraction buffer (EB) (0.1 M PIPES [pH 7.0], 0.5 mM $Na_2$EDTA, 0.5 mM $Na_2$EGTA, 5% ascorbic acid, 5 mM dithiothreitol [DTT], 5 mM thiourea, 12 mM L-cysteine HCl, 1% polyethylene glycol (PEG) 20,000, 0.1 mM phenylmethylsulfonyl fluoride [PMSF], and 20 g polyvinyl-polypyrrolidone [PVPP]). The slurry was homogenized for 10 min at medium speed, and then transferred into 250 mL centrifuge bottles and centrifuged at 23,000×g for 30 min in a GSA (Dupont-Sorvall) rotor.

The 350 mL crude supernatant obtained was brought to 40% ammonium sulfate (AS) saturation over 30 min by the addition of 79.86 g AS powder while being stirred in a beaker surrounded by an ice bath. The mixture was once again transferred to 250 mL centrifuge bottles and centrifuged at 23,000×g for 30 min as above. The 350 mL supernatant obtained was loaded into a 40 mL Macro-Prep (Bio-Rad) methyl hydrophobic interaction chromatography (HIC) column at the flow rate of 2.5 mL/min. All column fractions were monitored for protein using absorbance at 280 nm. The HIC column was washed with pre-equilibration buffer containing 1.7 M AS, 20 mM bis-tris-propane (pH 6.8), and 5 mM DTT until a baseline near zero was established. The column was then stripped with a buffer containing 10 mM (pH 7.0), 5 mM DTT, 1 mM $MgCl_2$. The first 15 mL out of column was discarded and the remaining eluate (200 mL) was loaded under gravity into a 100 mL Affi-Gel blue affinity gel (100–200 mesh, Bio-Rad) column that had the dye Cibacron blue F3GA covalently attached to the matrix. The gel was pre-equilibrated with 10 mM tris (pH 7.0), 5 mM DTT, 1 mM $MgC_2$ loading buffer. The column was washed extensively with this loading buffer until the baseline stabilized near zero, and the bound proteins were eluted with a buffer containing 10 mM tris (pH 7.0), 5 mM DTT, and 1.5 M sodium chloride (NaCl).

The 142 mL Affi-Gel Blue Gel column eluate was made 1.7 M AS by the slow addition of 31.8 g AS powder while being stirred for 30 min in a beaker surrounded by an ice bath. The slurry was centrifuged in 250 mL centrifuge bottles at 23,000×q for 30 min as above, and the supernatant loaded into a FPLC Phenyl-Sepharose column XK 26/20 (Pharmacia) at 23° C. The column was pre-equilibrated with a buffer containing 20 mM bis-Tris-Propane (pH 6.8), 5 mM DTT, and 1.7 M AS. When a baseline was established near zero the proteins were eluted out of the column in a 40 min reverse gradient of 1.7 M AS to 0 M AS at a flow rate of 5 mL/min, collecting 1 min fractions. The 0 M AS elution buffer contained 10 mM tris (pH 7.0), 5 mM DTT, and 1 mM $MgCl_2$.

Activity assays on the fractions collected indicated that the majority of enzymic activity for xanthosine-$N^7$-methyltransferase was concentrated in fractions 49 to 54. These fractions were pooled into 30 mL final volume, and then loaded into a 6 mL ATP-agarose column (Sigma Chemicals, A2767) by gravity at 4° C. The column was pre-equilibrated with 10 mM tris (pH 7.0), 5 mM DTT, and 1 mM $MgCl_2$. After stabilization of the baseline, the column was stripped with 20 mL of pre-equilibration buffer containing 100 µM xanthosine, and washed with an additional 40 mL pre-equilibration buffer. Both column eluates were pooled and loaded into a Mono-P HR 5/20 FPLC (Pharmacia) column pre-equilibrated with 25 mM bis-tris (pH 6.0) and 9% betaine at 23° C. After the baseline stabilized the column was eluted with 100 mL Polybuffer 74 (10 mL:90 mL $H_2O$, v:v) (pH 4.0) (Pharmacia), and 9% betaine at a flow rate of 1 mL/min. The collection tubes contained 100 µL 0.5 M tricine buffer (pH 7.0), and 50 mM DTT to give a final concentration in 1 mL of 50 mM tricine (pH 7.0), and 5 mM DTT in 1 min fractions. This in effect stabilized the final pH conditions for the proteins eluted under slightly acidic pH from the Mono-P column. The major activity for xanthosine-$N^7$-methyltransferase in collection tubes without tricine was found in fractions 15 and 16 of the gradient eluting from the column with a pH of 5.42 and 5.35 respectively. It was important not to freeze the protein samples at any stage of the purification, as this had a substantial negative effect on the activity state of xanthosine-$N^7$-methyltransferase.

B. Assay of Enzyme Activity.

The 100 µL standard assay mixture contained 50 mM tricine (pH 7.0), 1200 µM xanthosine, 5 mM DTT, 7.5 µM S-adenosyl-L-[methyl-$^{14}$C]-methionine (SAM) (60 mCi/mmol; DuPont MEN), and 1 mM $Na_2EDTA$. The reaction mixture (50 µL without enzyme) was preincubated for 10 min at 25° C. and the reaction was initiated by the addition of 50 µL enzyme solution and allowed to proceed at 25° C. for 1 hour. At the end of the incubation period three 30 µL aliquots of the reaction were removed and terminated by adding to 8 µL of 0.6 M perchloric acid ($HClO_4$). The same was done for zero time controls in order to detect true enzymic activity. This mixture was centrifuged in a microcentrifuge for 5 min and 19 µL of the supernatant was mixed with 1.0 µL of 33 mM 7-methylxanthosine. These mixtures were spotted on Whatman No. 1 chromatography paper and developed with n-butanol-acetic acid-$H_2O$ (n-BuOH-HOAc-$H_2O$)(4:1:1). The position of 7-methylxanthosine was determined by its blue fluorescence when exposed to short wavelength UV light. This region was cut out of the chromatograms and the radioactivity was determined by scintillation counting using 3 mL Scinti-verse scintillation fluid (Fisher Scientific). Counting efficiency was 74.7%. Background and non-specific radiation detected in the 7-methylxanthosine region of the zero time samples were subtracted.

C. Identification of the Reaction Product.

The site of methylation on the xanthine ring was identified by hydrolysis of the sugar from the methylated xanthosine reaction product and separation in 4 different chromatography systems. The product from two 100 µL reactions done as described above and containing 6 µL of 33 mM 7-methylxanthosine as carrier, was applied as a band at the origin of a Whatman No.1 paper chromatogram. The chromatogram was developed in n-BuOH-HOAc-$H_2O$ (4:1:1). The region of the chromatogram corresponding to methylated xanthosine was detected as above, cut into small pieces, placed in a sterile tube, and incubated with 35 mL of deionized water at 37° C. with shaking overnight. The extract was filtered through 2 layers of miracloth followed by a 0.22µ filter and then lyophilized. The dried extract was resuspended in 1.0 mL of deionized water, placed in a glass digestion vial and lyophilized. The sample was resuspended in 400µ of 1.0 M HCl and incubated for 1 hour at 100° C. The digest was lyophilized, resuspended in 400 µL of 3 mM 7-methylxanthine and again lyophilized. The digest was resuspended in 40 µL of deionized water, and 10 µl was chromatographed in each of four different systems. 1-Methylxanthine, 3-methylxanthine, 7-methylxanthine, 8-methylxanthine, 7-methylxanthosine, xanthine and xanthosine were included on each chromatogram for comparison. The following chromatography systems were used; Whatman No. 1 paper developed in n-BuOH-HOAc-$H_2O$ (4:1:1) and C8 thin layer plates (Whatman KC18F) developed in either isoamyl alcohol-$H_2O$-acetonitrile (41:4:5), ethanol-$H_2O$ (4:1) or tert-BuOH-HOAc-$H_2O$ (4:1:1). After drying, the chromatograms were sprayed with En$^3$Hance (Dupont NEN), redried and exposed for 30 days to pre-flashed Fuji RX$_{GCU}$ X-ray film at $-70°$ C.

D. Identification of Proteins by Gel Electrophoresis.

Extracts obtained as above were used in single dimension (ID) SDS-PAGE minigels (main gel:12.5% acrylamide, 0.8% methylene bisacrylamide; stacking gel:7.5% acrylamide, 0.21% methylene bisacrylamide) by mixing with Laemmli sample buffer (Laemmli, U.K., *Nature* 227:680 (1970)), and in two-dimensional (2D) mini IEF/SDS-PAGE by the modified method of O'Farrell et al. (O'Farrell, P. Z., Goodman, H. M., O'Farrell P. H., *Cell* 12:1133 (1977)). Two-dimensional electrophoresis was made possible by precipitating proteins with 50 volumes of 100% ethanol for 1 hour and redissolving the proteins in isoelectric focusing (IEF) sample buffer containing 5% ampholines (1:1, v:v, pH 3–10:pH 5–7, LKB-Pharmacia). The ratio of the original protein extract to the IEF sample buffer was maintained at least 1:2 to ensure that any remaining buffer constituents from the chromatography steps did not interfere with IEF. Equal total protein samples (<20 µg) were applied to the basic end of prefocused tube gels (8.8% acrylamide, 1.6% methylene bisacrylamide) containing 5% ampholines as above. The gels were focused for 10,000V-hours plus an additional 2 hours at 1,000 V. Blank focused gels were cut into 5 mm sections and incubated in 0.5 mL of 100 mM $CaCl_2$ for 24 hours, and the pH of the segments was determined. From this analysis, the pH gradient of the IEF gel was estimated to range from 4.4 to 6.0.

The tube gels were prepared for SDS-PAGE by a brief $H_2O$ wash followed by three washes (10 min each) in hot Laemmli sample buffer. The tube gels were placed on the top of SDS-PAGE gels (main gel:12.5% acrylamide, 0.8% methylene bisacrylamide; stacking is: gel:7.5% acrylamide, 0.21% methylene bisacrylamide) and held in place with 3% agarose in Laemmli sample buffer. Proteins were visualized by silver-staining. In 1D gels the Mono-P fraction 16 which had the highest enzymic activity indicated only the presence of a doublet under silver staining (FIG. 2). The molecular weight of these proteins in kilo-Daltons (kD) was approximately 37.6 and 36.1. In 2D gels each protein separated into two spots. The isoelectric point (IP) of the more acidic one had an average value over several gels of 5.2, and the more basic one of 5.3. Their molecular weights however now averaged 43.5 kD, with the upper and lower peptides fusing into each other. Therefore, there is a distinct difference in kD between 1D and 2D gels. The similar migration of all these four peptides in Mono-P columns, 1D and 2D gels indicates that they are isozymes which may be post-translationally modified. Alternatively they may be products of a gene family which have slight differences in their structure from each other, resulting in the differing isozymes observed.

E. Protein Sequencing.

Total protein estimation by the procedure of Lowry (Lowry, O. H., Rosebrough, N. J., Farr, A. L. and Randall, R. J., *J. Biol. Chem.* 193:265 (1951)) for fraction 16 of Mono-P indicated there was a total of 100 µg of protein in the 1 mL fraction. It is our experience that at these low concentrations of protein, Lowry values tend to be an over-estimation of the actual amount present. We decided to overcompensate for this by using a substantial part of this fraction for protein sequencing. A 900 µL portion of Mono-P fraction 16 representing 90 µg was placed in a sterile 1.5 mL microcentrifuge tube and 216 µL of 100% trichloro-acetic acid (TCA) was added to it. After mixing, the tube was allowed to incubate on ice overnight, and was then centrifuged at 14,000 rpm in a microcentrifuge for 30 min at 40° C. The supernatant was removed by aspiration, and the pellet washed twice with 1 mL of 75% ethanol, each washing being followed by a centrifugation step. The pellet was dried by placing the tube in a Speed Vac® and spinning for 1 min under vacuum. The precipitate had 20 µL of 2×Laemmli sample buffer added to it. It was then boiled in a water bath for 5 min, and then microfuged for 1 min. When the tube temperature had cooled down to 23° C. the whole amount was loaded into a single lane of a 12.5% 1D gel. At the termination of electrophoresis proteins were visualized by staining with 0.1% Coomassie R-250 in aqueous 50% methanol and 10% acetic acid, (w:v:v), and then destained. The same doublet of 37.6 and 36.1 kD observed in silver stained gels was also visible in the Coomassie stained gels. The region of the gel comprising this doublet was cut out and used for protein sequencing by automated Edman degradation.

Protein sequencing was performed by the University of California, Davis, Protein Structure Laboratory standard protocol. The gel piece containing the doublet was washed 4 times with 15 mL of $H_2O$ by shaking gently for 15 min to remove the acetic acid and SDS remaining from the previous steps. The gel piece was diced with a razor blade to 2 mm squares, and transferred to a 1.5 mL microcentrifuge tube. The gel pieces were dehydrated in a Speed-Vac for 2 hours until they did not adhere to the tube. Next 30 µL of gel rehydration buffer (0.1 M Tris-HCl, pH 9.0, 0.05% SDS) was added, and the pH verified at 8.0 by spotting 0.5 µL on pH paper. The digestion enzyme Lys-C (0.2 µg) from *Achromobacter lyticus* (Wako) was added, along with additional rehydration buffer to completely hydrate the gel pieces and leave a little extra buffer. The mixture was allowed to incubate overnight at 30° C. After the incubation period, the supernatant was removed to a fresh, sterile microcentrifuge tube and stored. Enough water was added to cover the gel pieces, and they were incubated for a further 2 hours at 30° C. The supernatant was removed and stored in the same microcentrifuge as before. This wash step was repeated once more, with the supernatants being combined with the previous two washes. The gel pieces were then covered with a solution comprising of 0.1% trifluoroacetic acid (TFA) in 80% acetonitrile, and incubated for 1 hour at 30° C. The supernatant was collected and added to the tube containing all the previous supernatants. The last wash was repeated once more, and the pooled supernatants were dried in a speed-vac.

The dried tryptic digestion products were dissolved in 25 µL of 6 M guanidine-HCl, 0.4 M tris (pH 8.2), and the pH verified by spotting 0.5 µL on pH paper. One µL of 450 mM DTT was added and the digest was incubated for 45 min at 50° C. After cooling to room temperature 2 µL of 500 mM iodoacetamide was added, and incubated for a further 15 min at 23° C. At the end of this incubation 72 µL of water was added to give a final concentration of 1.5 M guanidine, and 0.1 M tris. The sample was then centrifuged for 5 min at 14,000 rpm in a microcentrifuge and the supernatant was carefully removed to a new microcentrifuge tube. To the precipitated pellet 25 µL of 0.1% TFA was added and vortexed. The tube was then recentrifuged as before, and the supernatant added to that from the previous step.

The cleavage fragments from the tryptic digestion were resolved from each other by capillary high pressure liquid chromatography (HPLC) in a C18 1 mm×10 cm column, utilizing a linear gradient over 90 min of 5% solvent A (0.1% TFA) to 70% solvent B (0.075% acetonitrile) at a flow rate of 100 µL per min. The UV detection was set at 210 nm with the scale ranging from 0 to 0.1 A. The recovery of individual peaks indicated the presence of several distinct peptides as shown in FIG. 3. As a control a portion of the original BDS-PAGE gel that did not contain protein was carried through the digestion process. The filled peaks shown in FIG. 3 were common between this control and the sample. The three peaks labeled A, B, and C were subjected to automated Edman degradation. Two of the peaks (A and B) yielded overlapping unique sequences representing the same protein fragment (FIG. 4, Fragments A and B, SEQ ID NO:1 and SEQ ID NO:2, respectively). The third peak (C) yielded a different unique sequence (FIG. 4, Fragment C, SEQ ID NO:7).

F. Synthesis of Oligonucleotide DNA Primers for Xanthosine-$N^7$-methyltransferase.

Chemical synthesis of 20 mer primers for the two amino acid sequences obtained by the digestion fragments of xanthosine-$N^7$-methyltransferase was done by The Midland Certified Reagent Company. Regions of the fragments selected had minimal nucleic acid degeneracy, and where possible amino acids that have extensive genetic code redundancy were avoided. Where this was not possible more than one primer was synthesized for the same fragment to include all of the possible alternative codon combinations. Furthermore, we also synthesized primers such that they were complementary to the coding strand of the DNA sequences which code for the amino acid sequence. Third position nucleotide degeneracies of three or more were overcome by using inosine at these positions. Where the degeneracy of a nucleotide was two-fold, both nucleotides were included in primer synthesis (FIG. 4, SEQ ID NO:3, SEQ ID NO:4, SEQ ID NO:5, SEQ ID NO:6, SEQ ID NO:8, SEQ ID NO:9).

G. Extraction of RNA from B3 Stage Young Coffee Leaves.

All items used during the extraction were sterile, RNase-free, and prepared by treating with 0.1% DEPC water. All centrifugation steps were carried out at 4° C. unless otherwise stated.

Young coffee leaves of the B3 stage were collected and stored as previously described. Total RNA was isolated from 100 g of this young leaf tissue by grinding under liquid nitrogen and immediately transferring into a prechilled domestic coffee grinder. The tissue was ground to powder together with a small piece of dry-ice. The tissue was then added to 200 mL of homogenization buffer made up of 100 mM tris-HCl (pH 9.0), 200 mM NaCl, 15 mM $Na_2EDTA$, 0.5% sarcosyl, and freshly added 100 mM β-mercaptoethanol. To this was added 200 mL buffer-equilibrated phenol, and 40 mL of a mixture of chloroform:isoamyl alcohol (24:1, v:v). The tissue was then homogenized in a glass beaker in an ice bath for 2 min at high speed in a Polytron homogenizer. Immediately after homogenization 14 mL 3 M sodium acetate (pH 4.0) was added and mixed by operating the homogenizer for an additional 1 min. The homogenate was then stored on ice for 15 min., and subsequently transferred into two 250 mL polypropylene centrifuge tubes. Centrifugation was performed in a GSA (DuPont Sorvall) rotor at 16,000×g for 10 min. The aqueous phase (top layer) was transferred to a new 250 mL polypropylene centrifuge tube and an equal volume of isopropanol was added to it.

This mixture was incubated overnight at −20° C. and then centrifuged at 10,000×g for 10 min to collect the precipitated RNA.

The RNA pellet was washed with 70% ethanol and re-centrifuged at 10,000×g for 5 min. The ethanol was decanted and the pellet dried under vacuum for 5 min. The pellet was then resuspended in 15 mL of DEPC-treated water. The RNA suspension was transferred into a sterile 40 mL screw-cap centrifuge tube and the insoluble material removed by centrifugation at 10,000×g for 5 min. The supernatant was transferred to a new 40 mL screw-cap centrifuge tube and 5 mL of 8 M LiCl was added to it to give a final concentration of 2 M LiCl. The tube was incubated overnight at 4° C. and the RNA was recovered by centrifugation at 14,000×g for 10 min. The RNA pellet was then washed with 70% ethanol, centrifuged at 10,000×g for 5 min, and briefly dried under vacuum. The pellet was resuspended in 5 mL DEPC-treated water and centrifuged at 10,000×g for 5 min to remove insoluble material. The supernatant was transferred into 4 sterile 1.5 mL microcentrifuge tubes and stored on ice. The quantitation of 10 μL of the total RNA solution in a Shimadzu UV 160U spectrophotometer in a 230 to 330 nm spectrum indicated that there was 42.8 mg of RNA. The tubes containing the RNA were stored at −70° C.

H. Purification of Poly ($A^+$) mRNA from Total RNA.

The total RNA preparation was enriched for poly($A^+$) RNA (mRNA) using the PolyATtract II mRNA isolation system kit (Promega Corporation). A 600 μL aliquot of the total RNA equaling 5.1 mg was added into a tube of the above mentioned kit and made to 2.43 mL final volume with RNase-free water. After heating at 65° C. for 10 min, 10 μl of 50 pmole/mL biotinylated oligo(dT) and 60 μl of 20×SSC (175.3 g/L NaCl, 88.2 g/L sodium citrate, pH 7.0) were added and the mixture was allowed to slowly cool to room temperature over a period of approximately 30 min. An aliquot of the streptavidin paramagnetic particles were washed 3 times in 0.5×SSC (1.5 μL per wash) and resuspended in 0.5 mL of 0.5×SSC. The RNA solution containing the biotinylated oligo(dT) was added to the washed streptavidin paramagnetic particles. After a 10 min incubation at room temperature, the paramagnetic particles along with the trapped mRNA were captured to the side of the tube using a magnet. The supernatant was removed and the particles were washed four times with 0.1×SSC (1.5 mL/wash). The mRNA was recovered by suspending the particles in 1.0 mL RNase-free water and removing the water while the particles were captured on the side of the tube. The water was placed, 500 μL at a time, into two 1.5 mL sterile microcentrifuge tubes. After the addition of ⅟₁₀th volume of 3 M sodium acetate (50 μL per tube), the mRNA was recovered by precipitation with an equal volume of isopropanol (550 μL per tube). The tubes were stored at −20° C. overnight and then centrifuged at 14,000 rpm for 30 min at 4° C. The pellet was washed with 500 μL of 75% ice-cold ethanol and re-centrifuged. The ethanol was decanted and the pellet dried briefly under vacuum. The mRNA was dissolved in 60 μL of DEPC-treated nuclease-free sterile water. Quantitation was performed on 15 μL of the dissolved mRNA as described for total RNA. Approximately 9.6 μg of mRNA was recovered from 5 mg of total RNA.

I. Construction of cDNA Library

First and second strand cDNA was synthesized using the ZAP-cDNA synthesis kit (Stratagene). Four μg of mRNA in 25 μL of water was incubated at 65° C. for 5 min. Three μL of 100 mM methyl mercury was added and incubated at room temperature for 10 min. Four μL of 700 mM β-mercaptoethanol was added and incubation was continued for an additional 5 min. To the denatured mRNA 5 μL of 10× first strand buffer, 5 μL of 100 mM DTT, 3 μL nucleotide mixture (10 mM each dATP, dGTP, TTP and 5-methyl-dCTP), 2 μL of 1.4 μg/mL linker-primer (5'GAGAGAGAGAGAGAGAGAGAAC-
TAGTCTCGAGTTTTTTTTTTTTTTTTTT 3'), 1 μL RNase block and 5 μL of water were added. The reaction was incubated at room temperature for 10 min to anneal the primer to the mRNA and 2.5 μL of 20 u/μL M-MuLV reverse transcriptase was added. Five μL of this reaction mixture was removed to a tube containing 0.5 μL of 800 Ci/mmole [a-$^{32}$P]dCTP (DuPont NEN). Both reactions were incubated at 37° C. for 1 hour. The radioactively labeled reaction was frozen at −20° C. for later gel analysis.

To the 45 μL main reaction 40 μL of second strand buffer, 15 μL of 100 mM DTT, 6μL of nucleotide mixture (10 mM dATP, dGTP, TTP and 26 mM dCTP), 268.3 μL water and 2 μL of 800 Ci/mmol [a-$^{32}$-P)dCTP was added. After mixing, 4.5 μL of 1 u/μL RNase H and 19.2 μL of 5.2 u/μl E. coli DNA polymerase I were added and the reaction was incubated at 16° C. for 2.5 hours. The reaction was extracted with 400 μL of phenol:chloroform (1:1) and the phases were separated by centrifugation. The aqueous phase was removed to a new tube and re-extracted with chloroform. The aqueous phase recovered as above. The double-stranded cDNA was recovered by precipitation overnight at −200° C. after the addition of 33.3 μL of 3M sodium acetate and 867 μL of 100% ethanol. The precipitate was recovered by centrifugation in a microcentrifuge at 4° C. for 60 min. The precipitate was washed with 1 μL of 80% ethanol and recovered by centrifugation at room temperature at full speed in a microcentrifuge. The supernatant was removed, the precipitate was dried under vacuum and dissolved in 45 μL of water. Three μL of the resuspended double-stranded cDNA was removed and frozen at −20° C. until analyzed by gel electrophoresis.

To the remaining 42 μL of the double-stranded cDNA 5 μL of 10×Klenow buffer (buffer #3), 2.5 μL of 2.5 mM nucleotides (dCTP, dGTP, dATP and TTP), and 0.5 μL of 5 u/μL Klenow fragment were added. After 30 min at 37° C., 50 μL of water were added and the reaction was extracted with an equal volume of phenol:chloroform (1:1) and then chloroform as described above. After the addition of 7 μL of 3M sodium acetate and 226 μL of 100% ethanol, the blunt-ended double-stranded DNA was recovered by precipitation by incubating on ice for 30 min and microcentrifuging at full speed at 4° C. for 60 min. The pellet was washed with 300 μL of 80% ethanol, centrifuged and dried as before. Seven μL of 0.4 μg/μL EcoRI linkers were added to the dried cDNA. The structure of the EcoRI linkers is:

5'AATTCGGCACGAG 3'

3'GCCGTGCTC 5'

After vortexing to resuspend the cDNA, 1 μL of 10×ligation buffer, 1 μL 10 mM ATP and 1 μL of 4 Weiss u/μL T4 DNA ligase was added and the reaction was incubated over night at 8° C. The ligase was inactivated by heating at 70° C. for 30 min. The 5' ends of the EcoRI linkers attached to the cDNA were phosphorylated using polynucleotide kinase. One μL of 10×buffer #3, 2 μL of 10 mM ATP, 6 mL of water and 1 mL of 10 u/ML T4 polynucleotide kinase were added to the ligation reaction. After 30 min at 37° C. the kinase reaction was heat inactivated at 70° C. for 30 min.

XhoI "sticky ends" were generated at the end of the cDNA corresponding to the 3' end of the mRNA by digestion of the XhoI site in the linker-primer (see above). Twenty-eight μL of XhoI buffer and 3 μL of 40 u/mL XhoI were added to the cDNA and the reaction was incubated at 37° C. for 1.5 hours. The cDNA with EcoRI sticky ends at the 5' end and XhoI sticky ends at the 3' end (relative to the original mRNA) were size fractionated by passage through a Sephacryl S-400 spin column as follows. Five μL of 10×STE (100 mM tris (pH 7.0), 5 mM EDTA and 100 mM NaCl) was added and the cDNA was applied to the top of a 1 μL syringe containing Sephacryl S-400. A 500 ml microcentrifuge tube was placed on the bottom of the syringe and the column was placed in a centrifuge tube and centrifuged at about 400×g for 2 min. Sixty μL of 10×STE was added to the top of the syringe, a new microcentrifuge tube was placed on the bottom and the column was again centrifuged as before. This process was repeated until six fractions had been collected.

About 10% of each fraction was electrophoresed on a 1% agarose gel to determine the size distribution of the cDNA in each fraction. The remainder of each fraction was extracted with an equal volume of phenol:chloroform and then chloroform as described above and then precipitated by the addition of 2 volumes of 100% ethanol. After incubation at −200° C. over night, the cDNA was recovered by centrifugation at 14,000 rpm at 4° C. for 60 min in a microcentrofuge. The cDNA was washed with 200 μL of 80% ethanol as described above and dried. The cDNA was dissolved in 5 μL of water and 0.5 μL was removed to determine the cDNA concentration by fluorography using the Hoefer TKO 100 DNA Fluorometer. The remaining 4.5 mL of fraction 1, containing the largest cDNA molecules, contained about 304 ng of cDNA.

One-hundred ng of cDNA from fraction 1 was ligated into 1 μg of Uni-Zap, a bacteriophage lambda ZAP vector that had been digested with EcoRI and XhoI (Stratagene). Fraction 1 cDNA (2.9 Ml) was added to 0.54 μL of 10×ligation buffer, 0.5 μL 10 mM ATP, 1 μL of 1μg/μL Uni-Zap XR vector and 0.5 μL of 4 Weiss u/μL T4 DNA ligase. The reaction was incubated at 8° C. for about 44 hours. One μL aliquot of the ligation reaction was added to one aliquot of the 'Freeze-Thaw' extract from the Gigapack II Gold packaging kit (Stratagene). Fifteen μL of sonic extract was added and the contents were gently mixed. Packaging was carried out at room temperature. After 2 hours, 500 μL of SM buffer (0.01 M tris-HCL pH 7.5, 0.01 M $MgCl_2$ 0.1 mM $Na_2EDTA$) and 20 μL of chloroform was added to the packaging reaction, the debris was removed by a short centrifugation in a microcentrifuge and the packaged phages were stored at 4° C. until used.

J. Titering of Primary Library.

One μL of the 500 μL primary library was mixed with 9 μL of SM buffer for a 1/10 dilution. One μL of this dilution was used to infect 200 μL of E. coli XLI-Blue MRF' cells grown to a density equal to an $O.D._{.600}=0.5$. The cells were incubated at 37° C. for 15 min with gentle shaking. The infected cells were then mixed with 2.5 mL of 48° C. top agar containing 15 μL of 0.5 M IPTG, and 50 μL of 250 mg/mL X-gal and plated on 100×15 mm NZY plates (5 g/L NaCl, 2 g/L $MgSO_4.7H_2O$, 5 g/L yeast extract, 10 g/L NZ amine [pH 7.5], and 15 g Difco agar). The plates were incubated overnight at 37° C. Background plaques were blue, while the recombinant plaques were white. The average of three such plates indicated that 1 μL of primary library produced 1,930 white recombinant plaques, and 65 blue plaques. The total 500 μL primary library was calculated to represent 965,000 recombinant plaques.

K. Amplification of Primary Library.

Into 20 sterile tubes 300 μL of E. coli XLI-Blue MRF' cells grown to an $O.D._{.600}=0.5$ were added. To each tube 12.5 μL of primary library stock, and 90 μL of SM buffer were added and the tubes were incubated at 37° C. for 15 min. Two and one-half mL of 48° C. top agar was added to each tube and the cells were plated on 100×15 mm NZY plates. The plates were incubated overnight at 37° C. Five mL of SM buffer were added to each plate and the to plates were incubated for a further 8 hours at 4° C. The SM buffer was collected with a sterile pipette and stored in a sterile 250 mL centrifuge tube. Each plate was washed with about 4 mL of fresh SM buffer which was added to the previously collected material. Chloroform, to a final volume of 5%, was added to the amplified library. The library was then incubated at room temperature for 15 min and then centrifuged at 2,000×g for 10 min to remove cell debris. The supernatant (114.5 mL) was recovered and then transferred to a sterile polypropylene bottle. Chloroform was added to a final volume of 0.3% and the amplified library was stored at 4° C.

L. Titration of Amplified Library.

One μL of a $10^{-11}$ dilution of the amplified library in SM buffer contained 192 recombinant plaques when plated as described above. In order to obtain 50,000 recombinant plaques, 25 μL of a $10^{-7}$ dilution was used to infect 600 μL of E. coli XLI-Blue MRF' cells grown to an $O.D._{.600}=0.5$, which were then incubated at 37° C. for 15 min. To these cells 6.5 mL of 48° C. top agar was added and the library was plated on 150×15 mm NZY plates. Four such plates representing 200,000 recombinant plaques, were prepared and incubated at 37° C. overnight. The plates were then chilled for 4 hours at 4° C., and then used for DNA screening of the library.

M. Polymerase Chain Reaction (PCR) Amplification of xanthosine-$N^7$-methyltransferase cDNA.

The synthesis of first strand cDNA was as described in the Stratagene protocol above. The two unique peptide sequences obtained by tryptic digestion allowed the synthesis of the degenerate primers depicted in FIG. 4. A polymerase chain reaction (PCR) (Saiki, R. K., Gelfand, D. H., Stoffel, S., Scharf, S. J., Higuchi, R., Horn, G. T., Mullis, K. B. and Erlich, H. A., Science 239:487 (1988)) between pairs of these primers (1-6, 2-6, 3-5 or 4-5) using 4 ng cDNA, 1 μL 20 μM primers, 0.5 μL of each 1 mM deoxyribonucleotide triphosphate, 1.5 mM $MgCl_2$, 0.3 μL Taq DNA polymerase [5,000 u/mL], 2.5 μL 10×PCR buffer [10 mM tris-HCl (pH 9.0), 0.1% triton X-100] and sterile $H_2O$ to a final volume of 25 μL was carried out. PCR conditions were 94° C. for 4 min [1 cycle]; 94° C. for 1 min, 43° C. for 1 min, 7 cycles]; 72° C. for 5 min [1 cycle]). Reactions were done in 500 μL sterile microcentrifuge tubes is using a Perkin Elmer DNA thermal cycler 480. Only the primer combination 1 and 6 resulted in a single product at an annealing temperature of 43° C. The product was measured by agarose gel electrophoresis using SeaPlaque agarose (FMC) to be approximately 750 base pairs. A commercially available 100 bp ladder was used as a size marker (Promega Corporation).

N. Cloning of Coffee-specific Xanthosine-$N^7$-methyltransferase PCR Gene Product.

The 750 bp fragment obtained using primers 1 and 6 (FIG. 4) in a 50 μL PCR reaction had 50 μL of chloroform, and 100 μL of sterile water added to it. The mixture was vortexed and then centrifuged in a microcentrifuge at 14,000 rpm for 2 min. The top aqueous layer containing the DNA was removed and placed in a sterile tube. Ethidium-bromide plate quantitation indicated the presence of about 5 ng of PCR amplified DNA/μL. The PCR product was then ligated into a TA Cloning Kit pCR II vector (Invitrogen Corporation) in a 10 μL ligation reaction containing 1 μL 10×ligation buffer, 2 μL pCR II vector (25 ng/μL), 3 μL fresh PCR product (5 ng/μL), 1 μL T4 DNA Ligase, and 3 μL of sterile water. The ligation reaction was incubated at a 14° C. overnight. The ligation reactions were centrifuged at 14,000 rpm for 2 min and placed on ice. To a freshly thawed vial of *E. coli* XL1-Blue competent cells 2 μL of 0.5 M β-mercaptoethanol was added and mixed gently with the pipette tip. Two μL of the ligation reaction was pipetted into the cells and they were stirred gently with the pipette tip to mix. The vial was then incubated on ice for 30 minutes and heat shocked for exactly 30 seconds in a 42° C. heat-block. The vial was placed on ice. After 2 min 450 μL of sterile SOC medium (20 g/L tryptone, 5 g/L yeast extract, 0.5 g/L NaCl, 10 mL/L 250 mM KCl, 10 mL/L $MgCl_2$, 20 mL/L 1 M glucose, [pH 7.0]) was added to it. The vial was subsequently shaken at 225 rpm in a rotary shaker for I hour and then the placed on ice.

The transformed cells were plated by pipetting 50 μL and/or 200 μL from the cell suspension onto one of two LB plates (10 g/L tryptone, 5 g/L yeast extract, 10 g/L NaCl, 15 g/L Difco agar, pH 7.5) containing 50 μg/mL ampicillin and 40 μg/mL X-Gal. The plates were incubated at 37° C. for 20 hours and then moved to 4° C. for 3 hours to allow color development. Six white transformant colonies were analyzed for the presence and orientation of the PCR fragment.

O. Boiling Plasmid Mini-prep.

Each of the transformant colonies was grown in 5 mL sterile terrific broth (12 g/L tryptone, 24 g/L yeast extract, 4 mL/L glycerol, 100 mL/L 10×TB phosphate [0.17 M $KH_2PO_4$, 0.72 M $K_2HPO_4$]) supplemented with 50 μg/mL ampicillin. The tubes were incubated overnight in a rotary shaker at 37° C. Three mL of each colony was transferred to a 1.5 mL microcentrifuge tube, 1 mL at a time, and the cells concentrated by centrifugation at 14,000 rpm for 2 min. The supernatant was discarded each time and the cell pellet left as dry as possible. The cells were washed one time with 1 mL of sterile $H_2O$ and centrifuged as before. The supernatant was discarded and the cell pellet resuspended in 320 μL STET buffer (8% sucrose, 0.5% triton X-100, 50 mM EDTA, 10 mM tris-HCl, pH 8.0). To these cells, 32 μL of 10 mg/mL lysozyme in TE buffer (10 mL/L 1 M tris-HCl pH 8.0, 2 mL/L 0.5 M EDTA pH 8.0) was added and mixed by inverting the tubes several times. The tubes were placed in a boiling water bath for 5 min, and then placed immediately on ice. Once cooled they were centrifuged for 30 min at 14,000 rpm at 4° C. The pellet was removed from each tube with a sterile toothpick. The supernatant had 170 μL of 7.5 M $NH_4OAc$ and 550 μL of ice-cold isopropanol added to it, and the DNA was precipitated overnight at −20° C. The tubes were centrifuged at 14,000 rpm at 4° C. for 30 min, and the pellet washed with 75% ethanol and dried for 1 min in a speed-vac. The DNA was resuspended in 50 μL of sterile $H_2O$ containing 1 μL of 5 mg/mL RNase A.

P. Restriction Digestion to Remove Insert from pCR 11 Plasmid.

A reaction mixture of 25 μL was prepared by adding 15 μL of plasmid mini-prep DNA as obtained above, 2.5 μL of buffer H (90 mM tris-HCl [pH 7.5], 10 mM $MgCl_2$, 50 mM NaCl), 1 μL of EcoRI (8–12 u/μL), and 6.5 μL of sterile $H_2O$. The mixture was incubated in a shaking water bath at 37° C. for 1 hour, and then boiled in a water bath for 1 min. The tubes were centrifuged at 14,000 rpm for 15 seconds and then allowed to cool down to room temperature. To 10 μL of each mixture 2 μL of loading dye was added, and the digestion products were analyzed by 1.5% agarose gel electrophoresis using ultra-pure agarose (GibcoBRL) and a 100 bp ladder as a size marker (Promega Corporation).

Only one of the six reactions indicated the presence of a digested insert of ~750 bp. The original bacterial colony corresponding to the plasmid with the 750 bp xanthosine-$N^7$-methyltransferase PCR product was inoculated into a 250 mL Erlenmayer flask containing 50 mL of sterile LB media (10 g/L tryptone, 5 g/L yeast extract, 10 g/L NaCl, pH 7.5) supplemented with 50 μg/mL ampicillin. The flask was incubated in a rotary shaker at 30° C. overnight. In a 1.5 mL microcentrifuge tube 18 mL of the resulting cell media was concentrated by centrifugation as above.

Plasmid DNA was purified using the QIAGEN plasmid mini kit procedure (Qiagen Inc.). The washed bacterial pellet was resuspended in 0.3 mL of buffer P1 which contains the supplied RNase. To this 0.3 mL of alkaline lysis buffer P2 was added, mixed gently by flicking the tube and incubated for no longer than 5 min at room temperature. Next 0.3 mL of chilled buffer P3 was added and mixed by inverting the tube 6 times. After 10 minutes on ice the extract was centrifuged 14,000 rpm for 15 min in a microcentrifuge. The supernatant was removed and applied to a QIAGEN-tip 20 that was previously equilibrated by the application of 1 mL QBT buffer by gravity flow. The applied cell extract supernatant was also allowed to enter the resin of the column by gravity flow. Once the flow through the column had stopped, the QIAGEN-tip 20 was washed 4 times with one mL buffer QC. The DNA was eluted by washing the QIAGEN-tip 20 with 0.8 mL buffer QF and precipitated by the addition of 0.7 volumes (560 μL) of room temperature isopropanol. The tube was immediately centrifuged at 14,000 rpm for 30 min and the supernatant carefully removed. The precipitated DNA was washed with 1 mL of ice-cold 70% ethanol, centrifuged as above, and air dried for 5 min. The DNA was resuspended in 100 μL of sterile $H_2O$. UV spectrophotography, as described above, on 1 μL of the DNA resuspension indicated that there was 55 μg of purified recombinant pCRII plasmid DNA per 100 μL.

Automated DNA sequencing of the insert in the pCRII plasmid from its 5' end was accomplished using the M13 reverse primer which binds to a reference in pCRII just adjacent to the site where the PCR product was inserted. Sequencing was done at the University of Hawaii Biotechnology service facility. The sequencing reaction contained 1

µg of plasmid template and 3.2 pmol M13 primer. The sequence obtained indicated that the PCR product coded for the DNA sequence of the first 6 amino acids of peptide fragments A and B (FIG. 4) from whose sequence the degenerate DNA primers 1 and 2 (FIG. 4) were made. In addition, the sequence also coded for the following 7 amino acids of the peptide fragment, the DNA sequence of which was not used in primer construction. So in effect the DNA sequence for the correct protein was cloned.

Q. Making of a Random Primed Probe for cDNA Screening Using the PCR Product.

Two 25 µL restriction digestions with EcoRI were carried out on two 17.5 µL aliquots of the purified pCRII plasmid as described above. The products were separated on a 1% agarose gel as before, and the 750 bp insert was excised aseptically from two lanes of the gel. The gel pieces having a mass of 0.65 g were transferred into a sterile 40 mL polypropylene tube and subjected to Geneclean II kit purification (BIO 101, Inc). Four and one-half volumes of NaI (2.93 mL) stock solution was added to the gel slices. One-half the volume of the gel TBE modifier (325 µL) was added and the tube incubated at 45° C. for 5 min. To this 15 µL of glassmilk suspension was added and incubated for a further 5 min. The glassmilk/DNA complex was pelleted by centrifugation for 10 sec at 1,000 rpm and the supernatant was removed. The glassmilk pellet was washed 3 times with 1 mL New Wash solution and the DNA was eluted with 50 µL of sterile $H_2O$. Ethidium bromide plates indicated that the DNA concentration was 10 ng/µL.

A random primed probe was synthesized from 30 ng (3 µl) of the purified DNA. Three µl of the DNA was added to 27 µL of sterile water and the DNA was denatured by heating in a boiling water bath. To this the Promega Corporations Prime-a-Gene kit constituents (10 µL 5×labeling buffer, 2 µL of unlabeled dNTP's [20 µM each dCTP, dGTP, TTP), 2 µL 1 mg/mL acetylated BSA, 1 µL 5u/µL Klenow enzyme) and 5 µL of [$\alpha$-$^{32}$P]dATP (50 µCi, 3,000 Ci/mmole; DuPont NEN) were added to a final volume of 50 µL, and allowed to incubate at room temperature for 1 hour. The reaction was terminated by the addition of 2 µL 0.5 M $Na_2$EDTA (20 mM final concentration) and heated for 2 min in a boiling water bath.

R. Screening of Amplified Library with Random Primed Probe.

The four 150×15 mm NZY plates that had approximately 50,000 recombinant clones per plate were chilled to 4° C. (see above for plating and growth conditions), and the recombinant plaques lifted by first presoaking 132 mm Magna nylon transfer membranes (MSI Corporation) on chromatography paper saturated with 5×SSC buffer for paper saturated with 5×SSC buffer for 10 sec. The membranes were placed onto the plates containing the recombinant plaques for 5 min, and then lifted and placed, phage containing side up, for 2 min on chromatography paper saturated with 0.5 M NaOH and 1.5 M NaCl. The membranes were neutralized by transferring onto chromatography paper saturated with 0.5 M tris-HCl (pH 8.0) and 1.5 M NaCl for 5 min. They were then placed for 20 sec on chromatography paper saturated with 2×SCC buffer, 0.2 M tris-HCL (pH 7.5) and then blotted dry. After 1 hour of air drying, the DNA was cross-linked to the membranes by exposure to 12,000 µJoules of UV using a UV Stratalinker 1800 (Stratagene Corporation). The four membranes were prehybridized at 65° C. for 2 hours in 100 Ml 6×SSPE (52.2 g/L NaCl, 8.3 g/L $NaH_2PO_4.H_2O$ 2.2 g/L $Na_2$EDTA, [pH 7.4]), 5×Denhardt's solution (1 g/L Ficoll, 1 g/L polyvinylpyrrolidone, 1 g/L BSA [pentax fraction V]), 0.5% SDS and 100 µg/mL denatured herring sperm DNA in a Hybrid Mark II hybridization oven.

Hybridization was carried out at 65° C. for 12 hours in 10 mL of 6×SSPE, 0.5% SDS, 100 µg/mL powdered/denatured herring sperm DNA, and 52 µL ($15 \times 10^6$ dpms/mp) of the obtained random primed probe described above. At the end of the hybridization period the probe was removed and the membranes briefly washed for 30 sec with 100 mL of 65° C. 2×SSC containing 0.5% SDS. The membranes were then washed for an additional 30 min with the same amount and concentration of fresh buffer. The membranes were subjected to two or more 100 mL washes for 30 min with 65° C. 0.2×SSC, 0.5% SDS, and then wrapped in a cellophane envelope and exposed to pre-flashed Fuji $RX_{GCU}$ X-ray film at −70° C. for 24 hours. Fifteen positive clones were observed. These plaques were picked and placed in 1 mL SM buffer containing 20 µL chloroform (phage stock). Of these, 11 were processed to secondary or tertiary screening until single individual plaques were obtained.

S. Characterization of Xanthosine-$N^7$-methyltransferase cDNA Clones.

The sizes of the putative xanthosine-$N$-$^7$-methyltransferase cDNA clones were determined by polymerase chain reaction using primers homologous to the T3 and T7 promoters that are present in the cloning vector and that flank the cDNA insertion site. Conditions for polymerase chain reaction were as described above except that the cycle was 35 cycles of 95° C. for 1 minute, 50° C. for 1 minute and 72° C. for 2 minutes. Analysis agarose gel electrophoresis as before. The three largest clones obtained were subjected to in vivo excision by mixing in a sterile tube 200 µL of single plaque phage stock with 200 µL of fresh XL1-Blue MRF' cells grown to an O.D.$_{600}$=1.0. To this mixture 1 µL of ExAssist (Stratagene Corporation) helper phage (>$1\times10^6$ pfu/µL) was added and the tubes were incubated at 37° C. for 15 min. Three mL of sterile LB broth was added and incubation was continued for 3 hours at 37° C. with shaking. The cultures were heated in a 70° C. water bath for 20 min, and then the tubes centrifuged at 1,000×g for 15 min. One mL of the supernatant containing the excised pBluesript phagemid packaged as a filamentous phage particle was transferred to a sterile 1.5 mL microcentrifuge tube and stored at 4° C. as the stock solution. Twenty-five µL of the stock solution was added to 200 µL of E. coli Solar cells grown to an O.D.$_{600}$=1 in a microcentrifuge tube. After incubation at 37° C. for 15 min, the 200 µL cells were plated on 100×15 mm NZY agar plates containing 50 µg/mL ampicillin. The plates were incubated overnight at 37° C. until colonies appeared. A single colony was inoculated into 10 mL of sterile LB broth containing 50 µg/mL ampicillin and grown overnight at 37° C. with shaking. The 10 mL of cell culture was concentrated in a 1.5 mL sterile microcentrifuge tube and the pelleted cells subjected to QIAGEN plasmid purification as described previously. The purified plasmid DNA was resuspended in 50 µL of sterile $H_2O$. DNA automated sequencing reactions were performed by mixing 8 µL of this DNA sample (0.8 µg) with 4 µL of either T3 or T7 sequencing primers (0.8 pmol/µL). The remainder of the process was as previously described. Each sequencing reaction gave approximately 350 bases of sequence. The sequence is shown in FIG. 5 and SEQ ID NO:1 1. The amino acid sequence of xanthosine-$N^7$-methyltransferase as predicted from the base sequence of the cDNA is shown in FIG. 6 and SEQ ID NO:10.

T. Construction of Vectors for the Expression of Anti-Sense Xanthosine-$N^7$-Methyltransferase Transcripts The xanthosine-$N^7$-methyltransferase cDNA can be used to modify caffeine content in coffee by for example antisense expression or co-suppression. An example of its use with the vector pKR1 is described. This is only an example and many other plant transformation vectors could be used in conjunction with the xanthosine-$N^7$-methyltransferase cDNA. pKR1 was created by modification of pBI-121 (Clontech Laboratories) as follows.

Two 38-base pair synthetic sequences containing lox recognition sites for the cre site-specific recombinase were inserted surrounding the neomycin phosphotransferase II (NPT II) selectable marker gene of pBI-121. These lox sites allow for the removal of the NPT II gene from the construct after it is integrated into the plant genome [Dale and Ow, Proc. Natl. Aced. Sci. USA 88:10588 (1991)], but are not pertinent to the function of the xanthosine-$N^7$-methyltransferase cDNA in antisense.

Three synthetic oligonucleotides were synthesized based on the loxP sequences defined by Dale and Ow (supra). The sequence of these oligonucleotides are:

```
loxA: 5'-AGCTATAACTTCGTATAGCATACAT-
      TATACGAAGTTAT-3' loxB: 5'-AGCTATMCTTCGTATAATGTATGC-
      TATACGAAGTTAT-3', and loxc: 5'-ATAACTTCGTATAGCATACATTATAC-
      GAAGTTATAGCT-3'.
``` loxB is the complementary strand to both loxA and loxC. When loxA and loxB were annealed they formed a double-stranded molecule with 4-base overhangs complementary to HindIII overhangs which allows insertion of the double-stranded sequence into a HindIII site such as that found after the NOS transcription termination sequence adjacent to the NPT II gene in pBI-121. Annealing of loxC with loxB produces a blunt-ended double-stranded DNA containing a lox recognition site.

Synthetic lox sites were inserted surrounding the NPT II gene of pBI-121 as follows. pBI-121 was digested with PmeI (New England Biolabs, Beverly, Mass.) at 370° C. for 2 hours in reaction buffer supplied by the manufacturer. pBI-121 has a single PmeI site just proximal to the NOS promoter that drives expression of the NPT II gene. A synthetic lox site was generated by annealing equimolar amounts of IoxB and IoxC by heating at 95° C., slowly cooling to room temperature and ligating into the PmeI-digested pBI-121. The 30 μL ligation reaction contained ligation buffer (New England Biolabs, Beverly, Mass.), 60 nmoles PmeI-digested pBI-121, 3 μL of a 1 μM stock solution of annealed loxB/ loxC, 4 units PmeI and 4,000 units of high concentration T4 DNA ligase (New England Biolabs, Beverly, Mass.). Ligation was at 16° C. overnight. One to 4 μL of the ligation reaction were electroporated into E. coli XL1-Blue cells (Stratagene) and plated onto LB plates containing 50 μg/mL kanamycin, 50 μL of 20 mg/mL X-gal and 10 μL of 100 mM IPTG. White colonies were picked to fresh LB-kanamycin master plates.

Colonies containing the lox site were identified by colony hybridization. The master plates were grown for 4 hours at 37° C. and blotted to nylon membranes (MSI). The membranes were placed on fresh LB-kanamycin plates and grown at 37° C. overnight. The membranes were floated on 0.5 N NaOH for 10 minutes, neutralized by floating on 0.5 M Tris-HCl (pH 8.0) containing 0.5 M NaCL for 2 minutes and rinsed in 2×SSC.

The membranes were pre-hybridized in 20 mL of 6×SSPE, 5×Denhardt's solution, 0.5% SDS and 100 μg/mL fragmented herring sperm DNA at 55° C. for 3 hours. The pre-hybridization solution was replaced with 10 mL of fresh solution containing $8.4 \times 10^6$ cpm of IoxC labeled at the 5' end with [$^{32}$p] using T4 polynucleotide kinase. The 50 μL labeling reaction contained 50 pmoles of loxC, polynucleotide kinase reaction buffer (Promega), 15 μL of 3,000 Ci/mmol [y-$^{32}$P] ATP (DuPont-NEN) and 20 units T4 polynucleotide kinase (Promega). The reaction was incubated at 37° C. for 10 minutes and the product was separated from the unincorporated ATP using a Sephadex G-25 spin column. Hybridization was at 55° C. overnight. The filters were washed at 55° C. twice in 100 mL of 2×SSC containing 0.5% SDS, once with 100 mL of 1×SSC containing 0.5% SDS and autoradiographed as described previously.

Several colonies were found to hybridize intensely and were selected for further characterization. Plasmid DNA was extracted using the Magic Minipreps DNA Purification System® (Promega) and digested with PmeI as described above. Plasmids containing the lox site will no longer have a PmeI site. Plasmids that were resistant to digestion by PmeI were further analyzed by automated DNA sequencing at the University of Hawaii Biotechnology Service Center, to confirm insertion of a lox site.

A plasmid containing the lox site in the desired orientation was digested with HindIII, mixed with loxA/loxB heteroduplex that contains HindIII sticky-ends but not a complete HindIII restriction site, annealed as described above and ligated. The ligation reaction contained 2.5 ug of HindIII-digested plasmid, 1.25 pmoles of loxA/loxB, ligation buffer (Promega), 6 units of T4 DNA ligase (Promega), 1.25 units of HindIII (Promega) in a final volume of 30 μL. The reaction was incubated at room temperature for 1 hours, heated at 800C for 10 min and introduced into E coli XLI-Blue cells by electroporation (Stratagene). Random plasmids were screened for loss of the HindIII site by digestion with HindIII as above. Final confirmation of this plasmids structure, designated pKR1, was obtained by DNA sequencing as described above.

pKR1 was digested with SacI. The 173 μL reaction contained 10 μg pKR1, multicore buffer (Promega), and 20 units of SacI (Promega). After 1 hours at 37° C., 0.7 μL of 25 mM stocks of dATP, dCTP, dGTP and dTTP and 10 units of T4 DNA polymerase (Promega) were added. This reaction, which will make the SacI digestion products blunt-ended, was incubated at 15° C. for 30 minutes. After inactivation of the T4 DNA polymerase by incubation at 75° C. for 15 minutes, 24 units of SmaI were added and the reaction was incubated at room temperature for two hours. The reaction was stopped by heating at 80° C. for 15 minutes. The DNA was precipitated by the addition of 17 μL of 3 M sodium acetate and 375 μL of 100% ethanol. After 1 hours at −70° C. the DNA was recovered by centrifugation in a microcentrifuge at full-speed for 20 min at 4° C. The DNA was washed with 70% ethanol, dried under vacuum and dissolved in 88 μL water. Ten μL of 10×calf intestinal alkaline phosphatase buffer (Promega) and 20 units of calf intestinal alkaline phosphatase were added and the reaction was incubated at 37° C. for 2 hours. The reaction was stopped by the addition of 4 μL of 0.5 M EDTA and heating at 750C for 10 minutes. The sample was extracted with an equal volume of water saturated phenol, then with an equal volume of phenol:chloroform (1: 1) and finally with chloroform. The DNA was recovered by precipitation after adding 0.1 volume of 3 M sodium acetate and 2.5 volumes of 100% ethanol.

The coffee xanthosine-$N^7$-methyltransferase cDNA was released from the original plasmid by digestion with XhoI and BSaMI. Five jg of plasmid were digested in 100 μL containing 10 μL 10×Buffer D (Promega), 15 units XhoI, 1 μg of 10 mg/mL acetylated BSA. After incubation at 370C for 1 hours, 10 units of BSaMI were added and the reaction was continued at 65° C. After 1 hour at 65° C., 1 μL of each 10 mM dATP, dCTP, dGTP and dTTP and 15 units of T4 DNA polymerase (Promega) were added. The reaction was incubated at 37° C. for 5 minutes to make the DNA blunt-ended. After inactivation of the T4 DNA polymerase by incubation at 75° C. for 30 minutes, the volume was reduced to 55 μL in a Speed-Vac®. The digestion products were separated by electrophoresis on an 0.8% SeaPlaque agarose gel. The 1.3 kb coffee xanthosine-$N^7$-methyltransferase cDNA was recovered and purified using the Genclean II kit (Biol0l, Vista, CA). The cDNA was inserted into pKR1 by blunt-end ligation. A reaction volume of 20 μL contained ligation buffer (Promega), 1 μg pKR1, 150 ng cDNA and 20 units of T4 DNA ligase (Promega). The reaction was incubated at 8° C. for 72 hours. One μL of this ligation product was mixed with 20 μL of Nova Blue cells (Novagen) and incubated on ice for 30 minutes. The mixture was then heat-shocked for exactly 40 seconds in a non-shaking 42° C. water bath and then immersed on ice for 2 minutes. Eighty μL of room-temperature SOC buffer (Novagen) was added to the mixture. After incubation for 1 hour at 37° C. in a rotary shaker at 250 RPM, 50 μL of the mixture was plated into LB plates containing 40 μg/mL kanamycin and incubated overnight at 37° C. Seventeen colonies were selected for further analysis by PCR.

Each colony was touched with a sterile tooth-pick under aseptic conditions and transferred into a microcentrifuge tube containing 10 μL sterile Milli-Q water (cell dilution). The 25 μL PCR reactions contained 1 μL of the above cell dilutions, 1 μL each of 20 M 35S primer (5'-CCA CTA TCC TTC GCA AGA CC-3'), $MTR_2$ primer (5'-CAC AGT TAC CAT CTG CAG AT-3'), $MTL_4$ primer (5'-TGC TGG TGG ACA GTG TAT TC-3'), 0.5 μL of a 10 mM stock of each dATP, dCTP, dGTP and dTTP, 1.5 μL 25 mM $MgCl_2$, 2.5 μL 10×buffer (Promega), 0.3 μL 5 units/μL Taq DNA polymerase (Promega) and 16.2 μL sterile Milli-Q water. The PCR amplification conditions were 10 minutes at 94° C.; 35 cycles of 1 minute at 94° C., 1 minute at 50° C., 1 minute at 72° C., and 5 minutes at 72° C.

Sense orientation inserts gave the expected 723 bp PCR fragments with the 35S and $MTR_2$ primers. Antisense orientation inserts gave the expected 425 bp PCR fragments with the 35S and $MTL_4$ primers. One plasmid with the cDNA in the sense and one with the plasmid in the antisense direction were further analyzed by DNA sequencing of the junctions between the plasmid and cDNA to confirm the orientation. DNA sequencing was carried out as previously described. The antisense-containing plasmid, designated pKRCMTXA, is shown in FIG. 7.

FIG. 7 provides a schematic showing the construction of pKRCMTXA by the insertion of the xanthosine-$N^7$-methyltransferase coding region (MTX3A, in the antisense orientation) into the pKRl vector.

In addition to pKRCMTXA, a sense construct, pKRCMTXS, has also been recovered. The pKRCMTXS construct, illustrated in FIG. 8, contains the xanthosine-$N^7$-methyltransferase cDNA sequences (MTX3) in the opposite orientation relative to the orientation in pKRCMTXA. pKRCMTXA directs the expression of antisense transcripts and pKRCMTXS directs the expression of sense transcripts.

U. Electroporation of Agrobacterium with pKR1 Plasmid Containing the Xanthosine-$N^7$-Methyltransferase cDNA Gene in Sense (PKRCMTXS) and Antisense (pKRCMTXA) Orientation Agrobacterium strain LBA 4404 was grown from a single colony to $OD_{600}$ in 100 mL YM liquid media (0.4 g/L Yeast extract, 10 g/L mannitol, 0.1 g/L NaCl, 0.2 g/L $MgSO_4.7H_2O$), 0.5 g/L $K_2HPO_4$, pH 7.5) in a rotary shaker at 29° C. for 48 hours. The cells were concentrated by centrifugation at 4000×g to $6\times10^{11}$ cells/mL. Electroporation was performed using the "Electro Cell manipulator 600" (ECM 600, BTX Inc., CA). A 3.5 μL aliquot of either pKRCMTXA or pKRCMTXS plasmid solution containing 200 ng of DNA was mixed with 50 μL of concentrated Agrobactedum cells and transferred to a pre-cooled 2 mm gap cuvette (BTX Inc., CA) and a 5 ms pulse at 2.35 kV was applied. One mL of YM liquid media containing 50 μg/mL kanamycin was added to the electroporated cells and they were allowed to recover for 1 hour in a 29° C. shaker at 250 RPM. The cells were centrifuged at 4000×g and resuspended in 100 μL fresh YM liquid media. Transformed bacteria were selected on YM-agar plates (YM liquid media containing 15 g/L Bacto-agar) supplemented with 50 μg/mL kanamycin.

Confirmation of Agrobacterium transformation after incubation at 29° C. for 48 hours was obtained by picking 10 colonies from each transformation to fresh YM-agar/kanamycin plates on a marked grid. The presence and orientation of the xanthosine-$N^7$-methyltransferase gene insert was determined by PCR. A small amount of each colony was transferred to 20 μL sterile Milli-Q water using a sterile tooth-pick. PCR reactions were performed as described above using 1 μL of these cell suspensions as template DNA. For the sense orientation the 35S and $MTR_2$ primers were used and produced a product of the expected size, 723 bp. The antisense primers 35S and $MTL_4$ gave the expected product of 425 bp. We selected one colony of each orientation for transformation of coffee leaf tissue.

V. Infection of Coffee Leaf Tissue with Agrobacterium Containing the pKRCMTXS or pKRCMTXA Plasmid.

Mature young coffee leaves from plagiotrophic shoots were sterilized in 30% Clorox for 30 minutes and rinsed three times in sterilized distilled water. Approximately 7 $mm^2$ pieces from the lamina between the midrib and the margin were excised and placed in MS liquid media (Murashige and Skoog, 1962) with an Agrobactelium slurry of 109 cells/mL and co-cultvated for three hours. The leaf tissue was blotted dry with sterilized paper towels and co-cultivated with the remaining Agrobacterum for three days on MS media solidified by the addition of 2.0 g/L Phytagel.

The leaf tissue was again blotted with sterile paper towels to remove remaining Agrobacteria and then transferred into callus induction medium (MS medium containing 2,4-D and kinetin; Sondahl and Sharp, 1977), containing 500 μg/mL carbenecillin, and either 100 to 300 μg/mL kanamycin monosulfate or 10 to 20 μg/mL geneticin (G418). After 13 days of culture at 25° C. in the dark, primary callus started to appear.

W. Caffeine Production by Transformed Callus Cells

Caffeine content exuded by transformed or untransformed control cultures was assayed. Individual calli were maintained in 60×15 mm petri plates on 10 mL of solid media. After 30 days of culture in the dark, the calli were subcultured and the media were analyzed for caffeine. The media were extracted with chloroform and the caffeine content was measured by HPLC using a C18 reverse phase column and 98% 1.75 mM $H_2PO_4$, 1% acetonitrile and 1% tetrahydrofuran (THF) as the isocratic mobile phase. The flow rate was 2 mL/minute. The column was monitored at 210 nm and 260 nm. Caffeine was identified by its spectral properties and retention profile.

Caffeine production in transgenic coffee callus tissues in which the xanthosine-$N^7$-methyltransferase cDNA was inserted in the antisense orientation was reduced up to 98% compared with untransformed control callus tissues. Transformants contained from 26.0 pmoles of caffeine per mg tissue (fresh weight), which is the normal level, down to 0.24 pmoles of caffeine per mg tissue. It is known that variations can exist between independent transformants in the suppression of caffeine production. Therefore, independent transformants may be selected that produce a selected level of caffeine, or no caffeine, as desired.

X. Subculturing of Coffee Leaf Callus Tissue Containing the pKRMTXS or pKRMTXA Plasmids.

The antibiotic resistant calli were subcultured monthly using embryo induction media M II (basal salts, half-strength MS salts, 10 mg thiamine HCl, 40 mg cysteine HCl, 100 mg myo-inositol, 40 g sucrose, 2 mg BA, 1 mg pyridoxine, 1 mg nicotinic acid, 2.0 g phytagel, pH 5.65; Yasuda and Fujii, 1985) containing 300 μg/mL carbenecillin, and 150–200 μg/mL kanamycin for three months. These calli were then subcultured for thirty days into M II medium containing 100 μg/mL kanamycin, and for a further thirty days into M II medium containing 50 μg/mL kanamycin. Somatic embryos formed in this last medium. The somatic embryos developed into plantlets on germination media M III lacking growth regulators (basal salts, full-strength MS salts, 10mg thiamine HCl, 40 mg cysteine HCl, 100 mg myo-inositol, 40 g sucrose, 2 g phytagel, pH 5.65; Sondahl and Sharp, 1977) under fluorescent light.

The foregoing examples are for illustrative purposes only, and should not be viewed as limiting the scope of applicants' invention, which is set forth in the claims appended hereto.

We claim:

1. A coffee plant transformed with a nucleic acid sequence that codes on transcription for an RNA that is sense to the mRNA that codes on expression for xanthosine-$N^7$-methyltransferase, wherein the RNA has a length sufficient to interfere with the expression of a coffee plant xanthosine-$N^7$-methyltransferase.

2. The coffee plant of claim 1, wherein the xanthosine-$N^7$-methyltransferase comprises the amino acid sequence: (SEQ ID NO:10).

3. A coffee bean from the coffee plant of claim 1.

4. A coffee plant transformed with an isolated nucleic acid sequence that codes on expression for the amino acid sequence (SEQ ID NO:10), wherein the nucleic acid sequence is linked to a transcription promoter in a sense orientation.

5. A transformed coffee plant cell produced by the process of providing a transformation vector comprising a nucleic acid sequence that codes on transcription for a substantial run of RNA bases having the same base sequence as a base sequence of an RNA that codes for coffee plant xanthosine-$N^7$-methyltransferase, wherein the run of RNA bases has a length sufficient to interfere with the expression of xanthosine-$N^7$-methyltransferase in a coffee plant cell, and wherein the nucleic acid sequence is operably linked to a transcription promoter in a sense orientation; inserting the transforming vector into a coffee plant cell, wherein the nucleic acid sequence thereafter becomes inserted into the genome of the coffee plant cell to produce a transformed coffee plant cell.

6. The transformed coffee plant cell of claim 5, wherein the transformed cell exhibits reduced caffeine production compared to a coffee plant cell that is not transformed with the nucleic acid sequence.

7. A method for inhibiting production of caffeine by a coffee plant cell, comprising the steps of:
   providing a transforming vector comprising a nucleic acid sequence that codes on transcription for an RNA that has a length sufficient to interfere with the expression of a coffee plant xanthosine-$N^7$-methyltransferase, wherein the nucleic acid sequence is operably linked to a transcription promoter in an antisense orientation; and
   inserting the transforming vector into a coffee plant cell, wherein the nucleic acid sequence thereafter becomes inserted into the genome of the coffee plant cell to form a transformed cell, and wherein the transformed cell exhibits a 1% to 100% reduction in caffeine production compared to a coffee plant cell that has not been transformed with the nucleic acid sequence.

8. A transformed coffee plant cell produced by the method of claim 7.

9. The transformed coffee plant cell of claim 8, wherein the transformed cell exhibits greater than 97% reduction in caffeine production.

10. The transformed coffee plant cell of claim 8, wherein the transformed cell exhibits 10% to 90% reduction in caffeine production.

11. The transformed coffee plant cell of claim 10, wherein the transformed cell exhibits 25% to 75% reduction in caffeine production.

12. The transformed coffee plant cell of claim 11, wherein the transformed cell exhibits 50% reduction in caffeine production.

13. The transformed coffee plant cell of claim 8, wherein the coffee plant cell is *Coffea arabica*.

14. A coffee plant regenerated from the transformed coffee plant cell of claim 8.

15. A coffee bean from the coffee plant of claim 14.

16. A coffee plant cell transformed with an isolated nucleic acid sequence that codes on expression for the amino acid sequence: (SEQ ID NO:10), wherein the nucleic acid sequence is operably linked to a transcription promoter in a sense orientation.

17. The transformed coffee plant cell of claim 16, wherein the transformed cell exhibits reduced caffeine production compared to a coffee plant cell that is not transformed with the nucleic acid sequence.

18. A method for inhibiting production of caffeine by a coffee plant cell, comprising the steps of:

providing a transforming vector comprising a nucleic acid sequence that codes on transcription for a substantial run of RNA bases having the same base sequence as a base sequence of an RNA that codes for coffee plant xanthosine-$N^7$-methyltransferase, wherein the run of RNA bases has a length sufficient to interfere with the expression of a coffee plant xanthosine-$N^7$-methyltransferase, wherein the nucleic acid sequence is operably linked to a transcription promoter in a sense orientation; and inserting the transforming vector into a coffee plant cell, wherein the nucleic acid sequence thereafter becomes inserted into the genome of the coffee plant cell to form a transformed cell, and wherein the transformed cell exhibits a reduced caffeine production compared to a coffee plant cell that has not been transformed with the nucleic acid sequence.

19. A transformed coffee plant cell produced by the method of claim 18.

20. The transformed coffee plant cell of claim 19, wherein the transformed cell exhibits 1% to 100% reduction in caffeine production.

21. The transformed coffee plant cell of claim 20, wherein the transformed cell exhibits greater than 97% reduction in caffeine production.

22. The transformed coffee plant cell of claim 20, wherein the transformed cell exhibits 10% to 90% reduction in caffeine production.

23. The transformed coffee plant cell of claim 22, wherein the transformed cell exhibits 25% to 75% reduction in caffeine production.

24. The transformed coffee plant cell of claim 23, wherein the transformed cell exhibits 50% reduction in caffeine production.

25. The transformed coffee plant cell of claim 19, wherein the coffee plant cell is *Coffea arabica*.

26. A coffee plant regenerated from the transformed coffee plant cell of claim 19.

27. A coffee bean from the coffee plant of claim 26.

28. A transforming vector comprising a transcription promoter operably linked to (i) the nucleic acid sequence: (SEQ ID NO:11); or
(ii) a nucleic acid sequence that codes on expression for the amino acid sequence: (SEQ ID NO:10); or
(iii) a nucleic acid sequence that is an allelic variant of the nucleic acid sequence (SEQ ID NO;11),
wherein the nucleic acid sequence is linked to the transcription promoter in a sense orientation.

29. The transforming vector of claim 28, wherein the promoter is a cauliflower mosaic virus 35S promoter.

30. The method of claim 7, wherein the nucleic acid sequence codes on expression for the amino acid sequence: (SEQ ID NO:10).

31. The method of claim 18, wherein the nucleic acid sequence codes on expression for the amino acid sequence: (SEQ ID NO:10).

* * * * *

```
                        SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
        (A) LENGTH: 15 amino acid residues
        (B) TYPE: amino acid
        (C) STRANDEDNESS: N/A
        (D) TOPOLOGY: linear (ii) MOLECULE TYPE: <Unknown>
        (A) DESCRIPTION: peptide (v) FRAGMENT TYPE: Internal fragment (ix) FEATURE:
        (A) NAME/KEY: Fragment A
        (D) OTHER INFORMATION:  Xaa means undetermined (xi) SEQUENCE DESCRIPTION: SEQ ID NO: 1:

Ile Asn Tyr Ala Ser Gly Ala Ser Gly Ile Leu Asp Gln Xaa Gly
 1               5                  10                  15

(2) INFORMATION FOR SEQ ID NO: 2:

(i) SEQUENCE CHARACTERISTICS:
        (A) LENGTH: 14 amino acid residues
        (B) TYPE: amino acid
        (D) TOPOLOGY: linear (ii) MOLECULE TYPE: <Unknown>
        (A) DESCRIPTION: peptide (xi) SEQUENCE DESCRIPTION: SEQ ID NO: 2:

Ile Asn Tyr Ala Ser Gly Ala Ser Gly Ile Leu Asp Gln Thr
 1               5                  10

(2) INFORMATION FOR SEQ ID NO: 3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

(ii) MOLECULE TYPE: other nucleic acid
             (A) DESCRIPTION: primer (v) FRAGMENT TYPE: Internal fragment (ix) FEATURE:
             (D) OTHER INFORMATION: N is inosine (xi) SEQUENCE DESCRIPTION: SEQ ID NO: 3:

ATNAAYTAYG CNTCNGGNGC                                                    20

(2) INFORMATION FOR SEQ ID NO: 4:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nuclear acid
             (A) DESCRIPTION: primer (v) FRAGMENT TYPE: Internal fragment (ix) FEATURE (xi) SEQUENCE DESCRIPTION: SEQ ID NO: 4:

ATNAAYTAYG CNAGYGGNGC                                                    20

(2) INFORMATION FOR SEQ ID NO: 5:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid
             (A) DESCRIPTION: primer (v) FRAGMENT TYPE: internal (ix) FEATURE (xi) SEQUENCE DESCRIPTION: SEQ ID NO: 5:

CGNCCNGANG CRTARTTNAT                                                    20

(2) INFORMATION FOR SEQ ID NO: 6:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid
             (A) DESCRIPTION: primer (v) FRAGMENT TYPE: Internal fragment (ix) FEATURE (xi) SEQUENCE DESCRIPTION: SEQ ID NO: 6:

CGNCCRCTNG CRTARTTNAT                                                    20

(2) INFORMATION FOR SEQ ID NO: 7:

(i) SEQUENCE CHARACTERISTICS:
             (A) LENGTH: 14 amino acid residues
             (B) TYPE: amino acid

```
          (C) STRANDEDNESS: single
          (D) TOPOLOGY: linear (ii) MOLECULE TYPE: <Unknown>
          (A) DESCRIPTION: peptide (v) FRAGMENT TYPE: Internal fragment (ix) FEATURE (xi) SEQUENCE DESCRIPTION: SEQ ID NO: 7:

Gln Tyr Val Pro Cys Tyr Phe Xaa Phe Ile Asp Asp Gln Asp
 1               5                  10

(2) INFORMATION FOR SEQ ID NO: 8:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: other nucleic acid
          (A) DESCRIPTION: primer (v) FRAGMENT TYPE: Internal fragment (ix) FEATURE (xi) SEQUENCE DESCRIPTION: SEQ ID NO: 8:

CARTATGTNC CNTGTTATTT                                                      20

(2) INFORMATION FOR SEQ ID NO: 9:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: other nucleic acid
          (A) DESCRIPTION: primer (v) FRAGMENT TYPE: Internal fragment (ix) FEATURE (xi) SEQUENCE DESCRIPTION: SEQ ID NO: 9:

AARTARCANG GNACRTATTG                                                      20

(2) INFORMATION FOR SEQ ID NO: 10:

(i) SEQUENCE CHARACTERISTICS:
          (A) LENGTH: 371 amino acid residues
          (B) TYPE: amino acid
          (C) STRANDEDNESS: single
          (D) TOPOLOGY: linear (ii) MOLECULE TYPE: <Unknown>
          (A) DESCRIPTION: protein (xi) SEQUENCE DESCRIPTION: SEQ ID NO: 10:

Met Ala Phe Val Ala Arg Gln Trp Phe Leu Leu Ser Ile Ile Asn
 1               5                  10                  15

Val Val Val Val Cys Phe Leu Lys Pro Phe Ala Leu Gly Glu Gln
                20                  25                  30

Gln Val Pro Cys Tyr Phe Ile Phe Gly Asp Ser Gln Asp Asp Asn
                35                  40                  45

Gly Asn Asn Asn His Leu Asn Thr Thr Ala Arg Ala Asn Tyr Pro
```

```
                    50                  55                  60
Pro Tyr Gly Ile Asp Phe Pro Glu Gly Pro Thr Arg Phe Thr
                65                  70                  75
Asn Gly Arg Asn His Ala Asp Phe Ile Gly Glu Leu Leu Gly Phe
            80                  85                  90
Asp Ser Tyr Ile Pro Pro Phe Ala Asn Thr Lys Gly Arg Asp Ile
                95                  100                 105
Thr Lys Gly Ile Asn Tyr Ala Ser Gly Ala Ser Gly Ile Leu Asp
                110                 115                 120
Gln Thr Gly Arg His Leu Gly Asp Leu Phe Ser Phe Asn Glu Gln
                125                 130                 135
Leu His Asn His Glu Arg Ala Ile Ser Arg Ile Val Arg Leu Ile
                140                 145                 150
Gly Asn Arg Ser Ala Thr Lys Glu Tyr Leu Ala Lys Cys Leu Tyr
                155                 160                 165
Thr Val Ala Leu Gly Asn Asn Asp Tyr Ile Asn Asn Tyr Leu Leu
                170                 175                 180
Pro Glu Tyr Tyr Pro Thr Ser His Leu Tyr Thr Pro Arg Glu Phe
                185                 190                 195
Ala Ser Leu Leu Ile Arg His Tyr Ser Gln Gln Leu Arg Thr Leu
                200                 205                 210
Tyr Arg Leu Gly Ala Arg Lys Ile Ala Val Phe Gly Leu Gly Trp
                215                 220                 225
Leu Gly Cys Ile Pro Ala Glu Leu Ser Thr Asp Gly Asn Cys Val
                230                 235                 240
Asp Ser Ile Asn Glu Glu Val Leu Leu Phe Asn Asp Lys Leu Lys
                245                 250                 255
Pro Leu Val Asp Glu Leu Asn Thr Glu Leu Ser Gly Ala Gln Phe
                260                 265                 270
Leu Tyr Val Asp Val Ile Ala Ile Asn Leu Asn Asn Leu Ser Thr
                275                 280                 285
Pro Ala Glu Ile Thr Ile Gly Asn Ala Pro Cys Cys Asn Val Ser
                290                 295                 300
Ala Ala Val Ala Gly Gly Gln Cys Ile Pro Gly Gln Ile Pro Cys
                305                 310                 315
Ser Asn Arg Asn Gln Tyr Tyr Phe Trp Asp Asp Phe His Pro Ser
                320                 325                 330
Glu Val Val Asn Glu Ala Tyr Ser Arg Leu Ala Tyr Ser Ala Leu
                335                 340                 345
Ser Ser Leu Leu Asp Ala Asp Pro Leu Ala Ile Gly Gly Leu Thr
                350                 355                 360
Gly Lys Asn Cys His Asp Lys Val Lys Ile Gln
                365                 370

(2) INFORMATION FOR SEQ ID NO: 11:

(i) SEQUENCE CHARACTERISTICS:
        (A) LENGTH: 1347 base pairs
        (B) TYPE: nucleic acid
        (C) STRANDEDNESS: single
        (D) TOPOLOGY: linear (ii) MOLECULE TYPE: cDNA to mRNA (ix) FEATURE:
        (A) NAME/KEY:CDS
        (B) LOCATION:53..1168
```

(xi) SEQUENCE DESCRIPTION: SEQ ID NO: 11:

```
CCTCTGACTT GCTAAACCTA CCATTACCTT TTTCTTCTTG TCATCTGCAT TC              52

ATG GCT TTT GTA GCC AGG CAA TGG TTT CTC CTA TCC ATC ATT               94
Met Ala Phe Val Ala Arg Gln Trp Phe Leu Leu Ser Ile Ile
1               5                   10

AAT GTA GTG GTT GTC TGT TTC TTG AAA CCA TTT GCC CTA GGC              136
Asn Val Val Val Val Cys Phe Leu Lys Pro Phe Ala Leu Gly
 15                  20                  25

GAA CAA CAG GTC CCT TGC TAC TTC ATT TTT GGA GAC TCA CAA              178
Glu Gln Gln Val Pro Cys Tyr Phe Ile Phe Gly Asp Ser Gln
         30                  35                  40

GAT GAC AAT GGC AAC AAT AAT CAC CTG AAC ACC ACT GCC AGG              220
Asp Asp Asn Gly Asn Asn Asn His Leu Asn Thr Thr Ala Arg
             45                  50                  55

GCA AAT TAT CCA CCT TAC GGC ATT GAT TTC CCA GAA GGT CCA              262
Ala Asn Tyr Pro Pro Tyr Gly Ile Asp Phe Pro Glu Gly Pro
                 60                  65                  70

ACT GGT CGC TTC ACC AAT GGT CGA AAT CAT GCA GAC TTC ATT              304
Thr Gly Arg Phe Thr Asn Gly Arg Asn His Ala Asp Phe Ile
                     75                  80

GGT GAG CTC CTT GGA TTT GAC AGC TAC ATA CCT CCA TTT GCA              346
Gly Glu Leu Leu Gly Phe Asp Ser Tyr Ile Pro Pro Phe Ala
 85                  90                  95

AAT ACA AAA GGC CGG GAT ATC ACT AAA GGC ATT AAT TAT GCT              388
Asn Thr Lys Gly Arg Asp Ile Thr Lys Gly Ile Asn Tyr Ala
        100                 105                 110

TCG GGA GCA TCT GGA ATT CTT GAT CAG ACC GGT CGT CAC CTG              430
Ser Gly Ala Ser Gly Ile Leu Asp Gln Thr Gly Arg His Leu
            115                 120                 125

GGC GAT CTC TTC AGC TTC AAC GAA CAA TTG CAC AAT CAC GAG              472
Gly Asp Leu Phe Ser Phe Asn Glu Gln Leu His Asn His Glu
                130                 135                 140

AGA GCA ATT TCG CGC ATC GTG CGG TTG ATT GGA AAC AGA TCT              514
Arg Ala Ile Ser Arg Ile Val Arg Leu Ile Gly Asn Arg Ser
                    145                 150

GCA ACA AAA GAA TAT CTA GCC AAA TGT CTG TAC ACT GTT GCA              556
Ala Thr Lys Glu Tyr Leu Ala Lys Cys Leu Tyr Thr Val Ala
155                 160                 165

TTG GGG AAT AAT GAT TAC ATC AAC AAC TAC TTG TTG CCA GAA              598
Leu Gly Asn Asn Asp Tyr Ile Asn Asn Tyr Leu Leu Pro Glu
        170                 175                 180

TAT TAT CCT ACC AGC CAC CTA TAT ACT CCA AGA GAA TTT GCC              640
Tyr Tyr Pro Thr Ser His Leu Tyr Thr Pro Arg Glu Phe Ala
            185                 190                 195

AGC TTG TTA ATT AGG CAT TAT TCT CAG CAA CTA CGG ACT TTG              682
Ser Leu Leu Ile Arg His Tyr Ser Gln Gln Leu Arg Thr Leu
                200                 205                 210

TAC AGA TTG GGG GCA AGA AAA ATA GCC GTT TTT GGG CTT GGT              724
Tyr Arg Leu Gly Ala Arg Lys Ile Ala Val Phe Gly Leu Gly
                    215                 220

TGG CTT GGC TGC ATA CCT GCT GAG TTA TCT ACA GAT GGT AAC              766
Trp Leu Gly Cys Ile Pro Ala Glu Leu Ser Thr Asp Gly Asn
225                 230                 235

TGT GTG GAT TCT ATT AAC GAG GAA GTT CTG TTA TTC AAT GAC              808
Cys Val Asp Ser Ile Asn Glu Glu Val Leu Leu Phe Asn Asp
        240                 245                 250

AAG CTC AAG CCA CTG GTT GAT GAA CTG AAT ACC GAG TTA AGC              850
Lys Leu Lys Pro Leu Val Asp Glu Leu Asn Thr Glu Leu Ser
```

-continued

| | | | | |
|---|---|---|---|---|
| | 255 | 260 | 265 | |
| GGT GCA CAA TTT CTT TAT GTA GAT GTG ATA GCA ATC AAT TTG<br>Gly Ala Gln Phe Leu Tyr Val Asp Val Ile Ala Ile Asn Leu<br>270 275 280 | | | | 892 |
| AAC AAT TTA TCC ACC CCT GCA GAA ATT ACA ATT GGC AAT GCA<br>Asn Asn Leu Ser Thr Pro Ala Glu Ile Thr Ile Gly Asn Ala<br>285 290 | | | | 934 |
| CCA TGC TGC AAC GTG TCT GCA GCA GTT GCT GGT GGA CAG TGT<br>Pro Cys Cys Asn Val Ser Ala Ala Val Ala Gly Gly Gln Cys<br>295 300 305 | | | | 976 |
| ATT CCT GGG CAA ATT CCC TGC AGC AAC AGG AAC CAA TAT TAT<br>Ile Pro Gly Gln Ile Pro Cys Ser Asn Arg Asn Gln Tyr Tyr<br>310 315 320 | | | | 1018 |
| TTT TGG GAT GAT TTC CAT CCC AGT GAA GTA GTC AAT GAA GCA<br>Phe Trp Asp Asp Phe His Pro Ser Glu Val Val Asn Glu Ala<br>325 330 335 | | | | 1060 |
| TAT TCA AGA TTA GCA TAT TCT GCG TTA TCC TCA TTA CTT GAT<br>Tyr Ser Arg Leu Ala Tyr Ser Ala Leu Ser Ser Leu Leu Asp<br>340 345 350 | | | | 1102 |
| GCT GAT CCT CTT GCC ATT GGC GGC CTA ACA GGC AAA AAC TGT<br>Ala Asp Pro Leu Ala Ile Gly Gly Leu Thr Gly Lys Asn Cys<br>355 360 | | | | 1144 |
| CAT GAT AAA GTG AAG ATA CAA TAGACTGTAT CTATGTGTCC<br>His Asp Lys Val Lys Ile Gln<br>365 370 | | | | 1185 |
| CATGATATTT CTATATTCCA AGTTTCCGAC AAGTCAAACT CAATGTAATA | | | | 1235 |
| AAACTTGAGA GTCCGAATGT GCTAGTGTGA TGTTATCTCC TCAATGGAAA | | | | 1285 |
| CAATATGTTA TCATTAATCT CAGACTATTT ATAATTACTA TTAAAAAAAA | | | | 1335 |
| AAAAAAAAAA AA | | | | 1347 |